United States Patent
Iio et al.

(10) Patent No.: US 8,945,056 B2
(45) Date of Patent: Feb. 3, 2015

(54) INJECTION DEVICE WITH PUNCTURE FUNCTION, METHOD FOR CONTROLLING INJECTION DEVICE WITH PUNCTURE FUNCTION, CHEMICAL SOLUTION ADMINISTRATION DEVICE, AND METHOD FOR CONTROLLING CHEMICAL SOLUTION ADMINISTRATION DEVICE

(75) Inventors: Toshiaki Iio, Ehime (JP); Yoshinori Amano, Ehime (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 190 days.

(21) Appl. No.: 13/426,998

(22) Filed: Mar. 22, 2012

(65) Prior Publication Data

US 2012/0179016 A1 Jul. 12, 2012

Related U.S. Application Data

(62) Division of application No. 11/522,971, filed on Sep. 19, 2006, now Pat. No. 8,202,249.

(30) Foreign Application Priority Data

Sep. 20, 2005 (JP) .................................. 2005-271629
Sep. 20, 2005 (JP) .................................. 2005-271632

(51) Int. Cl.
| | |
|---|---|
| *A61M 1/00* | (2006.01) |
| *A61M 5/145* | (2006.01) |
| *A61B 5/15* | (2006.01) |
| *A61B 5/145* | (2006.01) |
| *A61M 5/172* | (2006.01) |
| *A61M 5/14* | (2006.01) |

(52) U.S. Cl.
CPC .......... *A61M 5/14566* (2013.01); *A61B 5/1411* (2013.01); *A61B 5/14532* (2013.01); *A61M 5/1723* (2013.01); *A61M 2005/1402* (2013.01); *A61M 2205/52* (2013.01); *A61M 2230/201* (2013.01)
USPC ........................................................ 604/152

(58) Field of Classification Search
CPC .......... A61M 5/14566; A61M 5/1452; A61M 5/14216; A61B 5/14532; A61B 5/14865
USPC .................................................. 604/152–156
See application file for complete search history.

(56) References Cited

U.S. PATENT DOCUMENTS

| | | |
|---|---|---|
| 4,008,717 A | 2/1977 | Kowarski |
| 5,148,811 A | 9/1992 | Messinger |
| 5,325,867 A | 7/1994 | Skrabal et al. |

(Continued)

FOREIGN PATENT DOCUMENTS

| | | |
|---|---|---|
| JP | 2002-219114 | 8/2002 |
| JP | 2004-555 | 1/2004 |

*Primary Examiner* — Nicholas Lucchesi
*Assistant Examiner* — Melissa A Snyder
(74) *Attorney, Agent, or Firm* — Wenderoth, Lind & Ponack, L.L.P.

(57) ABSTRACT

An injection device with a puncture function includes, in a single casing, a cylindrical cartridge in which insulin is enclosed, a cartridge holder to which the cartridge is inserted, a needle inserted at a front end of the cartridge, a reciprocation unit for reciprocating the cartridge toward the needle, and an extrusion member for extruding the insulin from a rear end of the cartridge toward the needle, and the motion speed and the motion amount of the reciprocation unit are made variable.

15 Claims, 15 Drawing Sheets

(56) References Cited

U.S. PATENT DOCUMENTS

| | | | |
|---|---|---|---|
| 5,529,463 A | 6/1996 | Layer et al. | |
| 5,902,253 A | 5/1999 | Pfeiffer et al. | |
| 5,993,412 A | 11/1999 | Deily et al. | |
| 6,056,716 A | 5/2000 | D'Antonio et al. | |
| 6,175,752 B1 | 1/2001 | Say et al. | |
| 6,268,910 B1 | 7/2001 | Samsoondar et al. | |
| 6,547,755 B1 * | 4/2003 | Lippe et al. | 604/67 |
| 7,258,672 B2 | 8/2007 | Hansson et al. | |
| 7,276,027 B2 | 10/2007 | Haar et al. | |
| 7,481,787 B2 | 1/2009 | Gable et al. | |
| 2004/0073123 A1 | 4/2004 | Hessel et al. | |
| 2004/0234380 A1 * | 11/2004 | Moutafis et al. | 417/53 |
| 2005/0080345 A1 | 4/2005 | Finburgh et al. | |
| 2005/0177398 A1 | 8/2005 | Watanabe et al. | |
| 2006/0184051 A1 | 8/2006 | Hempstead et al. | |

* cited by examiner

INJECTION DEVICE WITH PUNCTURE FUNCTION, METHOD FOR CONTROLLING INJECTION DEVICE WITH PUNCTURE FUNCTION, CHEMICAL SOLUTION ADMINISTRATION DEVICE, AND METHOD FOR CONTROLLING CHEMICAL SOLUTION ADMINISTRATION DEVICE

CROSS-REFERENCE TO RELATED APPLICATION

This application is a divisional of U.S. application Ser. No. 11/522,971, filed Sep. 19, 2006, now U.S. Pat. No. 8,202,249 the entirety of which is incorporated herein by reference.

FIELD OF THE INVENTION

The present invention relates to an injection device with a puncture function, a method for controlling the injection device with a puncture function, a chemical solution administration device, and a method for controlling the chemical solution administration device.

BACKGROUND OF THE INVENTION

A diabetic patient measures his/her blood glucose level periodically, and injects insulin on the basis of the blood glucose level to keep a normal blood glucose level. Conventionally, in order to measure blood glucose level, a small amount of blood is collected from a finger tip or the like of a patient using a puncture unit, and next, the blood glucose level of the collected blood is measured using a measurement unit, and thereafter, insulin is injected into the patient according to the measured blood glucose level using an injection unit.

More specifically, as shown in FIG. 17, initially a puncture needle port 2 of a puncture unit 1 is applied to a finger tip or the like of a patient. Thereafter, a button 3 is pressed. Then, a needle protrudes from the puncture needle port 2 at high speed and goes back instantly, whereby the needle makes a minute wound on the finger tip or the like, and blood is collected from this wound.

Then, using a measurement unit 4 for measuring blood glucose level shown in FIG. 18, the collected blood is dropped onto a sensor 5 that is inserted in the measurement unit 4. Thereby, the blood glucose level is displayed on a display 6. On the basis of the blood glucose level displayed on the display 6, an amount of insulin to be administered is set by a setting button 8 of an injection unit 7 shown in FIG. 19.

Next, a puncture needle port 9 of the injection unit 7 is applied to the skin of the patient, and an administration button is pressed. Then, a needle protrudes from the puncture needle port 9 and thereby insulin is administrated to the patient. As prior arts relating to the present invention, Japanese Published Patent Application No. 2002-219114 (Patent Document 1) and Japanese Published Patent Application No. 2004-000555 (Patent Document 2) are known.

In the conventional administration of insulin, however, since the puncture unit 1, the measurement unit 4, and the injection unit 7 are different units independent from each other, it is troublesome to take along all of these units.

SUMMARY OF THE INVENTION

The present invention is made to solve the above-described problems and provides an injection device with puncture function that can be easily taken along, a method for controlling the injection device with puncture function, a chemical solution administration device, and a method for controlling the chemical solution administration device.

Other objects and advantages of the invention will become apparent from the detailed description that follows. The detailed description and specific embodiments described are provided only for illustration since various additions and modifications within the scope of the invention will be apparent to those of skill in the art from the detailed description.

According to a first aspect of the present invention, an injection device with puncture function including, in a single casing, a cartridge in which a chemical solution is enclosed, and having a needle inserted at a front end thereof; a cartridge holder into which the cartridge is inserted; a reciprocation means for reciprocating the cartridge and the cartridge holder; and an extrusion means for extruding the chemical solution from a rear end of the cartridge toward the needle; wherein the reciprocation means reciprocates the cartridge and, at this time, a motion speed and an amount of motion of the reciprocation means are variable, and puncture by the needle or administration of the chemical solution through the needle is carried out.

According to a second aspect of the present invention, in the injection device with puncture function according to the first aspect, the extrusion means comprises a first motor, a first rpm/linear motion conversion unit which is disposed between a rotation axis of the first motor and a piston that pushes the rear end of the cartridge, and a first rpm detection unit for detecting a rpm of the first motor.

According to a third aspect of the present invention, in the injection device with puncture function according to the second aspect, the first rpm/linear motion conversion unit comprises a first shaft having an external thread at its surface, and a baffle-shaped unit to which a first nut having an internal thread that fits the external thread is fixed, the baffle-shaped unit being formed integrally with the piston.

According to a fourth aspect of the present invention, in the injection device with puncture function according to the second aspect, the first rpm detection unit comprises a first encoder that is connected to the rotation axis of the first motor, and a first sensor for detecting a rpm of the first encoder.

According to a fifth aspect of the present invention, in the injection device with puncture function according to the third aspect, an elastic extension member is inserted between the first shaft and the first nut.

According to a sixth aspect of the present invention, in the injection device with puncture function according to the second aspect, the first motor, the first rpm/linear motion conversion unit, and plural gears provided between the first motor and the first rpm/linear motion conversion unit are arranged in a horseshoe shape.

According to a seventh aspect of the present invention, in the injection device with puncture function according to the first aspect, the reciprocation means comprises a second motor, a second rpm/linear motion conversion unit which is connected between a rotation axis of the second motor and a rear end of a frame on which the extrusion means is mounted, and a second rpm detection unit for detecting a rpm of the second motor.

According to an eighth aspect of the present invention, in the injection device with puncture function according to the seventh aspect, the second rpm/linear motion conversion unit comprises a second shaft having an external thread at its surface, and the frame to which a second nut having an internal thread that fits the external thread is fixed.

According to a ninth aspect of the present invention, in the injection device with puncture function according to the seventh aspect, the second rpm detection unit comprises a second encoder that is connected to the rotation axis of the second motor, and a second sensor for detecting a rpm of the second encoder.

According to a tenth aspect of the present invention, in the injection device with puncture function according to the first aspect, the needle is a hollow needle made of metal, and the needle serves both as a puncture needle to be used for puncture, and as an administration needle to be used for administration of the chemical solution.

According to an eleventh aspect of the present invention, in the injection device with puncture function according to the first aspect, the reciprocation means is moved at a high speed by a small distance during puncture, while it is moved at a low speed by a large distance during extrusion of the chemical solution.

According to a twelfth aspect of the present invention, the injection device with puncture function according to the first aspect further includes a power supply switch for turning on and off a power supply, the switch being disposed in approximately the center of a casing of the device.

According to a thirteenth aspect of the present invention, the injection device with puncture function according to the first aspect further includes a touch sensor for detecting that the device touches the skin of a patient, the sensor being disposed next to a puncture needle port through which the needle moves in and out.

According to a fourteenth aspect of the present invention, the injection device with puncture function according to the first aspect communicates, with a measurement device that measures a blood glucose level, data of the measured blood glucose level, using a communication means.

According to a fifteenth aspect of the present invention, in the injection device with puncture function according to the fourteenth aspect, the communication means performs communication using light.

According to a sixteenth aspect of the present invention, in the injection device with puncture function according to the first aspect, the reciprocation means comprises a magnet and a coil.

According to a seventeenth aspect of the present invention, in the injection device with puncture function according to the sixteenth aspect, the reciprocation means includes a linear encoder in addition to the magnet and the coil.

According to an eighteenth aspect of the present invention, in the injection device with puncture function according to the sixteenth aspect, the reciprocation means comprises a guide pin for guiding a frame on which the extrusion means is disposed so as to move the frame linearly, a magnet and a coil for driving the frame so as to move the frame linearly, the magnet and coil being attached onto an outer circumference of the frame, and a linear encoder for detecting a movement distance of the frame.

According to a nineteenth aspect of the present invention, a method for controlling the injection device with puncture function according to the first aspect, comprises a first step of moving the needle forward at a high speed by a small distance, using the reciprocation means; a second step of moving the needle backward to its original position at a high speed, using the reciprocation means, after the first step; a third step of setting an amount of extrusion of the chemical solution, after the second step; a fourth step of moving the needle forward at a low speed by a large distance, using the reciprocation means, after the third step; a fifth step of extruding the chemical solution from the needle by the amount that is set in the third step, using the extrusion means, after the fourth step; and a sixth step of moving the needle backward to its original position at a low speed, using the reciprocation means, after the fifth step.

According to twelfth aspect of the present invention, the control method according to the nineteenth aspect further includes a seventh step of moving the needle forward at a low speed by a large distance using the reciprocation means, between the third step and the fourth step; an eighth step of extruding air in the cartridge from the needle using the extrusion means, after the seventh step; and a ninth step of moving the needle backward to its original position at a low speed using the reciprocation means, after the eighth step.

According to a twenty-first aspect of the present invention, a chemical solution administration device comprises, in a single casing, a connector to which a blood sensor is connected; an analysis unit for analyzing components in blood, to which a signal inputted to the connector is supplied; a display unit connected to an output of the analysis unit; a control unit to which required signals are supplied from an input unit; an extrusion means having one input to which an output of the control unit is connected, and the other input to which an output of a memory is connected; a cartridge to which an output of the extrusion means is connected, the cartridge having a chemical solution enclosed therein and a needle inserted at a front end thereof; and a reciprocation means having one input to which the output of the control unit is connected, and the other input to which the output of the memory is connected; wherein the output of the analysis unit is connected to the input of the memory to store the analysis result obtained by the analysis unit into the memory, and the output of the reciprocation means is connected to the needle.

According to a twenty-second aspect of the present invention, in the chemical solution administration device according to the twenty-first aspect, the extrusion means comprises a first motor, a first rpm/linear motion conversion unit which is disposed between a rotation axis of the first motor and a rear end of the cartridge, and a first rpm detection unit for detecting a rpm of the first motor.

According to a twenty-third aspect of the present invention, in the chemical solution administration device according to the twenty-second aspect, the first rpm/linear motion conversion unit comprises a first shaft having an external thread at its surface, and a first nut which is fixed to a piston, and has an internal thread that fits the external thread.

According to a twenty-fourth aspect of the present invention, in the chemical solution administration device according to the twenty-second aspect, the first rpm detection unit comprises a first encoder that is connected to the rotation axis of the first motor, and a first sensor for detecting a rpm of the first encoder.

According to a twenty-fifth aspect of the present invention, in the chemical solution administration device according to the twenty-third aspect, an elastic extension member is inserted between the first shaft and the first nut.

According to a twenty-sixth aspect of the present invention, in the chemical solution administration device according to the twenty-second aspect, the first rpm/linear motion conversion unit is arranged in a horseshoe shape.

According to a twenty-seventh aspect of the present invention, in the chemical solution administration device according to the twenty-first aspect, the reciprocation means comprises a second motor, a second rpm/linear motion conversion unit which is connected between the second motor and a frame, and a second rpm detection unit for detecting a rpm of the second motor.

According to a twenty-eighth aspect of the present invention, in the chemical solution administration device according to the twenty-seventh aspect, the second rpm/linear motion conversion unit comprises a second shaft having an external thread at its surface, and a second nut which is fixed to the frame, and has an internal thread that fits the external thread.

According to a twenty-ninth aspect of the present invention, in the chemical solution administration device according to the twenty-seventh aspect, the second rpm detection unit comprises a second encoder that is connected to the rotation axis of the second motor, and a second sensor for detecting a rpm of the second encoder.

According to a thirtieth aspect of the present invention, in the chemical solution administration device according to the twenty-seventh aspect, the needle is a hollow needle made of metal, and the needle serves both as a puncture needle to be used for puncture, and as an administration needle to be used for administration of the chemical solution.

According to a thirty-first aspect of the present invention, in the chemical solution administration device according to the twenty-first aspect, an insertion port into which a blood sensor is inserted is provided on an outer wall of the casing, the outer wall being different from a wall where a puncture needle port through which the needle goes in and out is provided.

According to a thirty-second aspect of the present invention, in the chemical solution administration device according to the twenty-first aspect, the reciprocation means is moved at a high speed by a small distance during puncture, while it is moved at a low speed by a large distance during extrusion of the chemical solution.

According to a thirty-third aspect of the present invention, the chemical solution administration device according to the twenty-first aspect further includes a power supply switch for turning on and off a power supply, the switch being disposed in approximately the center of the casing.

According to a thirty-fourth aspect of the present invention, the chemical solution administration device according to the twenty-first aspect further includes a touch sensor for detecting that the device touches the skin of a patient, the sensor being disposed next to a puncture needle port through which the needle goes in and out.

According to a thirty-fifth aspect of the present invention, a method for controlling the chemical solution administration device according to the twenty-first aspect comprises a blood collection step of collecting blood; a measurement step of analyzing the collected blood, after the blood collection step; a storage step of storing data measured by the measurement step into a memory, after the measurement step; and an administration step of administrating a chemical solution after the storage step.

According to a thirty-sixth aspect of the present invention, in the control method according to the thirty-fifth aspect, an air releasing step is inserted before the administration step.

According to a thirty-seventh aspect of the present invention, in the control method according to the thirty-fifth aspect, a correction step of correcting the data measured in the measurement step is inserted after the storage step.

According to a thirty-eighth aspect of the present invention, in the control method according to the thirty-fifth aspect, after administration of the chemical solution is carried out in the administration step, the needle is moved backward when a predetermined waiting time has passed.

An injection device with puncture function according to the present invention includes, in a single casing, a cartridge in which a chemical solution is enclosed, and having a needle inserted at a front end thereof; a cartridge holder into which the cartridge is inserted; a reciprocation means for reciprocating the cartridge and the cartridge holder; and an extrusion means for extruding the chemical solution from a rear end of the cartridge toward the needle; wherein the reciprocation means reciprocates the cartridge and, at this time, a motion speed and an amount of motion of the reciprocation means are variable, and puncture by the needle or administration of the chemical solution through the needle is carried out. Therefore, the function of the puncture device for collecting blood and the function of the injection device for administrating the chemical solution are included in the same casing, thereby realizing an injection device with puncture function which can be easily taken along.

Further, according to the present invention, since the needle for collecting blood and the reciprocation means for reciprocating the needle are commoditized, miniaturization of the device can be realized.

Further, according to the present invention, the result of analysis operation performed by the analysis unit is automatically stored as it is in the memory. Accordingly, it is not necessary for the patient to enter the data using the setting button of the injection device. Moreover, since the data is automatically stored in the memory, no setting error occurs.

Further, according to the present invention, since the data is automatically stored in the memory, the patient is saved from the burden of setting.

Further, according to the present invention, the function of the puncture device for collecting blood, the function of the measurement device for measuring the property of the blood, and the function of the injection device for administrating the chemical solution are included in the same casing, whereby the injection device with puncture function can be easily taken along.

Further, according to the present invention, since the needle for blood collection and administration of chemical solution, and the reciprocation means for reciprocating the needle, are commoditized, miniaturization of the device can be achieved.

DETAILED DESCRIPTION OF THE INVENTION

Hereinafter, embodiments of the present invention will be described with reference to the drawings.

Embodiment 1

Figure 1:
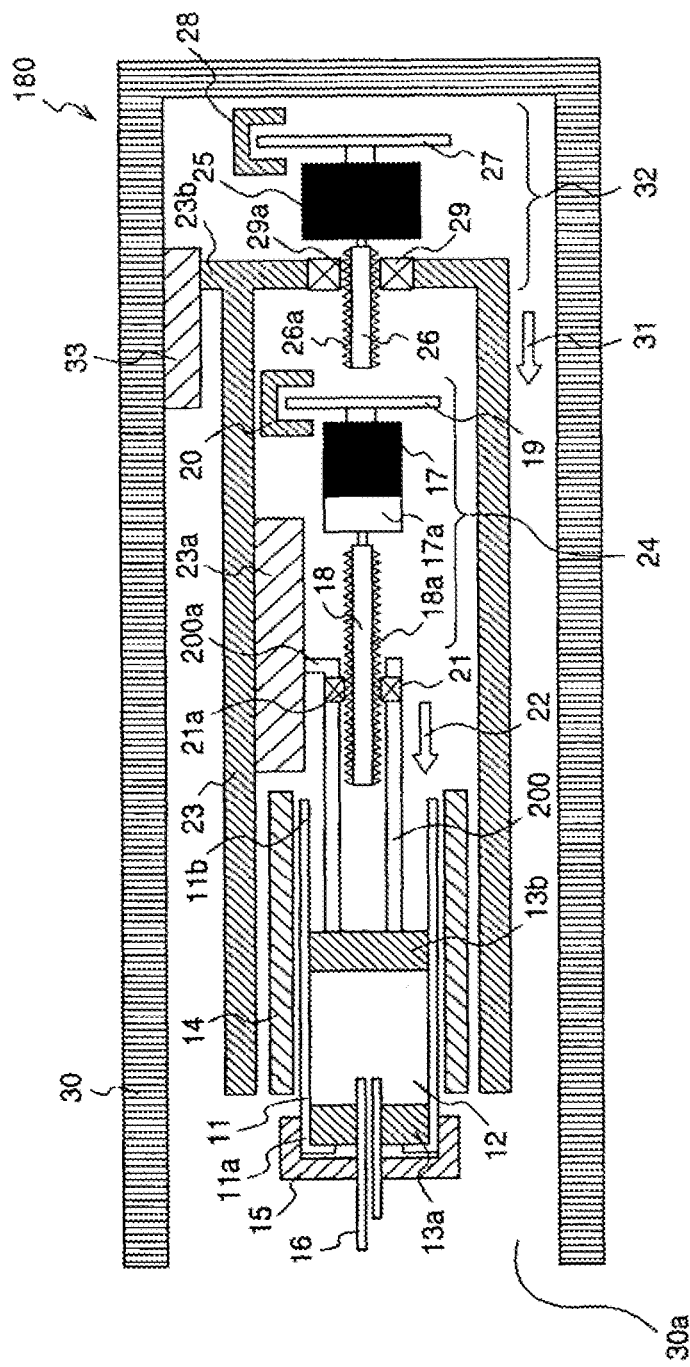
FIG. 1 is a cross-sectional view of an injection device with puncture function according to a first embodiment of the present invention.

FIG. 1 is a cross-sectional view illustrating an injection device with puncture function according to a first embodiment of the present invention.

With reference to FIG. 1, reference numeral 11 denotes a cylindrical cartridge in which insulin 12 adopted as an example of a chemical solution is enclosed, and rubber stoppers 13a and 13b are inserted at a front end 11a and a rear end 11b of the cartridge 11, respectively.

Reference numeral 14 denotes a cartridge holder into which the cartridge 11 is inserted. The cartridge 11 is attached to the cartridge holder 14, and a circular cap 15 is attached to the front end of the cartridge 11. The cartridge 11 and the cap 15 are detachable from the cartridge holder 14. A hollow needle 16 comprising metal is set in approximately the center of the cap 15. A root side of the needle 16 penetrates the stopper 13a that is inserted at the front end 11a of the cartridge 11, and reaches the insulin 12.

Reference numeral 17 denotes a DC (direct current) motor that is used as a power for extruding the insulin 12 toward the needle 16. A rotation axis of this motor 17 is connected to a shaft 18 through a deceleration mechanism 17a comprising a gear. An external thread is formed at the surface of the shaft 18.

Figure 2:
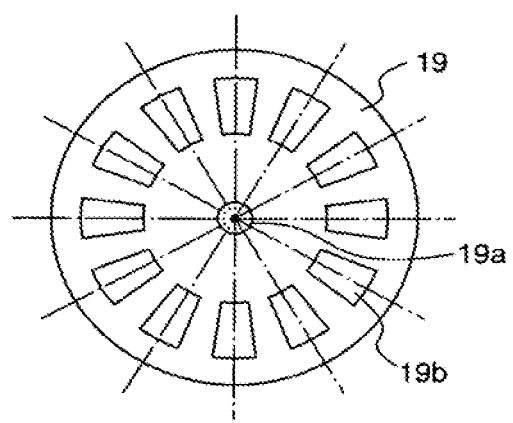
FIG. 2 is a plan view of an encoder for measuring rpm, according to the first embodiment.

Reference numeral 19 denotes an encoder provided in conjunction with the rotation axis of the motor 17, and numeral 20 denotes a transmissive sensor for detecting rotation (rotation amount and rotation speed) of the encoder 19. The sensor 20 is not necessarily of a transmissive type, it may be a reflective sensor. Further, the encoder 19 is a circular plate in shape as shown in FIG. 2. Reference numeral 19a denotes the center of rotation of the encoder 19, and numeral 19b denotes holes that are provided on an inner concentric circle in the vicinity of an outer circumference of the encoder 19. The encoder 19 has twelve holes 19b arranged at regular intervals. The encoder 19 rotates with rotation of the motor 17. Then, optical signals transmitted through the holes 19b and optical signals shielded by the holes 19b are outputted as pulse signals from the sensor 20.

Accordingly, by counting the pulse signals, the number of rotations of the motor 17, and the number of rotations (including rotation angle) of the shaft 18, as well as the rotation speeds thereof can be easily measured.

Turning to FIG. 1, reference numeral 21 denotes a nut that is fixed in conjunction with a piston 200, and an internal thread 21a that fits the external thread 18a formed on the shaft 18 is formed inside the nut 21. The nut 21 may be integrated with the piston 200. Reference numeral 200a denotes a convex portion of the piston 200, which is formed integrally with the piston 200. A piston guide 23a regulates rotation of the convex portion 200a, and guides the convex portion 200a in the horizontal direction.

Accordingly, when the motor 17 rotates in the positive direction, the shaft 18 and the encoder 19 rotate, and the rotational motion of the shaft 18 cooperates with the nut 21 to move the piston 200 in the forward direction shown by an arrow 22 (toward the attached needle 16).

The distance in which the piston 200 moves can be measured by counting the pulse signals outputted from the sensor 20.

Further, the speed at which the piston 200 moves can be measured by the density (frequency) of the pulse signals outputted from the sensor 20.

The front end of the piston 200 contacts the stopper 13b that is inserted into the cartridge 11. The stopper 13b is provided slidably from the rear end 11b of the cartridge 11 toward the front end 11a of the cartridge 11, and the stopper 13b in the cartridge 11 is extruded in the direction of the arrow 22 when the piston 200 advances in the direction of the arrow 22. That is, the insulin 12 is discharged from an end of the hollow needle 16.

When the first motor 17 is reversely rotated, the piston 200 moves backward in the direction opposite to the arrow 22.

Reference numeral 23 denotes a frame to which the first motor 17 is fixed, and this frame 23 is provided so as to enclose the first motor 17 and the cartridge holder 14. The first motor 17, the deceleration mechanism 17a, the first shaft 18, and the first nut 21 constitute an extrusion means or member 24 for extruding the chemical solution from the rear end 11b of the cartridge 11 toward the needle 16. Further, the frame 23 constitutes the piston guide 23a.

Reference numeral 25 denotes a DC motor, and this second motor 25 is used as a power for reciprocating the extrusion means 24 disposed on the frame 23 and the cartridge 11 having the needle 16. A rotation axis of this second motor 25 is connected to a second shaft 26. An external thread 26a is formed at the surface of the second shaft 26.

Reference numeral 27 denotes a second encoder that is provided in conjunction with the rotation axis of the second motor 25, and numeral 28 denotes a transmissive sensor for detecting rotation (rotation amount and rotation speed) of the second encoder 27. This second sensor 28 is not necessarily of a transmissive type, and it may be a reflective sensor. Further, like the first encoder 19, the second encoder 27 rotates with rotation of the second motor 25.

Then, rotation information of the second encoder 27 (rotation amount and rotation speed) is outputted as pulse signals from the second sensor 28. Accordingly, by counting the pulse signals, the number of rotations of the second motor 25, and the number of rotations (including the rotation angle) of the second shaft 26, as well as the rotation speeds thereof can be measured.

Reference numeral 29 denotes a second nut that is fixed in conjunction with the frame 23, and an internal thread 29a that fits the external thread 26a formed on the second shaft 26 is provided inside the second nut 29. A frame convex portion 23b is formed in the frame 23, and it is guided by a rail formed on a casing 30.

Accordingly, when the second motor 25 rotates in the positive direction, the second shaft 26 and the second encoder 27 rotate in the positive direction. That is, the rotation of the second shaft 26 cooperates with the second nut 29 to move the frame 23 in the forward direction shown by an arrow 31. The distance in which the frame 23 moves can be detected by the number of pulse signals outputted from the second sensor 28. Further, the speed at which the frame 23 moves can be detected by the density (frequency) of the pulse signals outputted from the second sensor 28.

Further, when the second motor 25 is rotated in the reverse direction, the second shaft 26 and the second encoder 27 rotate in the reverse direction. Then, the frame 23 moves in the direction opposite to the arrow 31 (moves backward) by the function of the rotating second shaft 26 and the second nut 29. The movement distance can be detected by counting the number of pulse signals outputted from the second sensor 28, and the movement speed can be detected by the density (frequency) of the pulse signals outputted from the second sensor 28.

That is, since the second shaft 26 is connected to the frame 23 through the second nut 29, when the second motor 25 rotates in the positive direction, the second frame 23 moves forward in the direction of the arrow 31, whereby the entirety of the cartridge 11 including the needle 16, which is connected to the extrusion means 24, moves forward. Conversely, when the second motor 25 rotates reversely, the frame 23 moves in the direction opposite to the arrow 31, i.e., moves backward, whereby the entirety of the cartridge 11 including the needle 16, which is connected to the extrusion means 24, moves backward.

As described above, it is possible to reciprocate the frame 23 by rotating the second motor 25 in the positive direction or the reverse direction, and thereby, it is possible to reciprocate the extrusion means 24 constituted on the frame 23 as well as the entirety of the cartridge 11 including the needle 16, which is connected to the extrusion means 24. The second motor 25, the second shaft 26, the second nut 29, the frame convex portion 23b, the rail 33, the second encoder 27, and the second sensor 28 constitute the reciprocation means or unit 32.

That is, the frame convex portion 23b is formed outward from the frame 23, while the rail 33 into which the frame convex portion 23b is fitted is formed on the casing 30. Accordingly, the frame convex portion 23b slides on the rail 33. That is, the cartridge 11 including the needle 16 and the frame 23 joined with the cartridge 11 reciprocate in the direction of the arrow 31 and in the reverse direction. At this time, due to the effect of the frame convex portion 23b and the rail 33, the cartridge 11 and the frame 23 do not rotate with respect to the casing 30. Further, in the normal state, the tip of the needle 16 is hidden in a puncture needle port 30a that is formed at the front end of the casing 30. Accordingly, the needle 16 is usually invisible from the outside, thereby reducing patient's fear.

Figure 3:
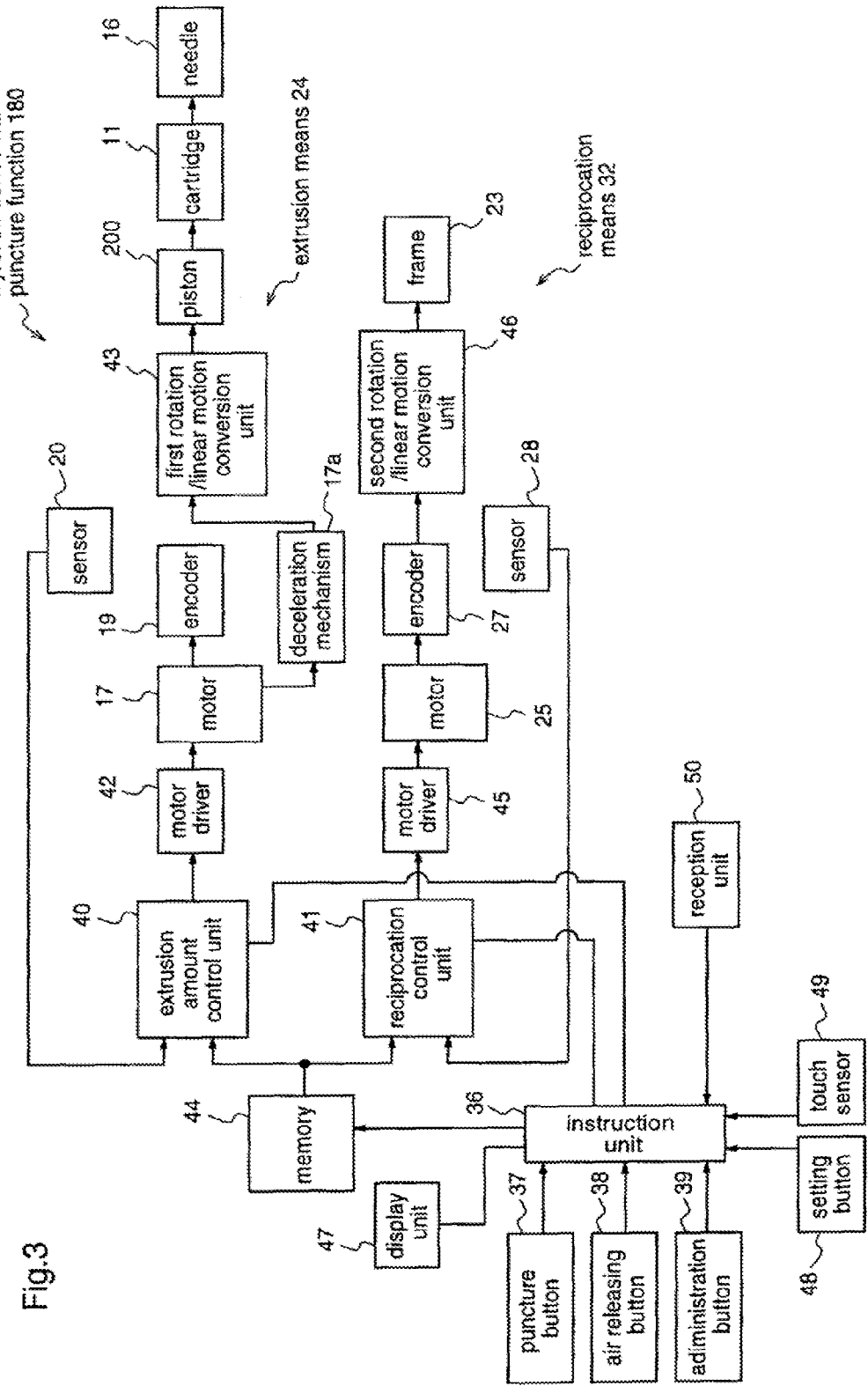
FIG. 3 is a block diagram of an injection device with puncture function according to the first embodiment.

FIG. 3 is a block diagram illustrating the construction of the injection device with puncture function 180 according to the first embodiment of the present invention. With reference to FIG. 3, reference numeral 36 denotes an instruction unit for instructing, for example, positive rotation/reverse rotation, and low speed/high speed of the first motor 17. A puncture button 37, an air releasing button 38, an administration button 39, a setting button 48, a touch sensor 49, and a reception unit 50 are connected to the input of the instruction unit 36.

The instruction unit 36 is also connected to a display unit 47. The display unit 47 is used for checking the amount of insulin 12 that is set by using the setting button 48. The set amount is stored in a memory 44.

The touch sensor 49 is a sensor for detecting that the puncture needle port 30a of the injection device with puncture function 180 touches the skin of the patient, and it is either a mechanical switch or a photo sensor. In this first embodiment, a mechanical switch is used.

The reception unit 50 receives data of blood glucose level that is transmitted from a transmission unit 140 of a measurement device 130 which will be later described as a fourth embodiment, and the blood glucose level data is stored in the memory 44.

The output of the instruction unit 36 is connected to a control input of an extrusion amount control unit 40 that is a component of the extrusion means 24, a control input of a reciprocation control unit 41 that is a component of the reciprocation means 32, and an input of the display unit 47. An output of the control unit 40 is connected to the first motor 17 through the motor driver 42. An output of the first motor 17 is connected to the first encoder 19 and to a first rpm/linear motion conversion unit 43 that is constituted by the first shaft 18 and the first nut 21. An output of the first rpm/linear motion conversion unit 43 is connected to the needle 16 through the piston 200 and the cartridge 11.

Reference numeral 20 denotes a first sensor for detecting the rpm of the first encoder, and the output of the first sensor 20 is connected to the input of the control unit 40. Further, the output of the memory 44 is also connected to the input of the control unit 40.

The output of the control unit 41 is connected to the second motor 25 through the motor driver 45. The output of the second motor 25 is connected to the second encoder 27 and to a second rpm/linear motion conversion unit 46 that is constituted by the second shaft 26 and the second nut 29. The output of the second rpm/linear motion conversion unit 46 is connected to the frame 23 on which the extrusion means 24 is placed. Reference numeral 28 denotes a second sensor for detecting the rpm of the second encoder 27, and the output of the second sensor 28 is connected to the input of the controller 41. Further, the output of the memory 44 is also connected to the input of the control unit 41.

Next, the operation of the injection device 180 with puncture function according to the first embodiment will be described hereinafter.

Initially, the puncture button 37 is pressed to collect blood from a patient. At this time, when the touch sensor 49 touches the skin of the patient, the instruction unit 36 informs the control unit 41 that the puncture button 37 is pressed. The control unit 41 obtains, from the memory 44, the number of rotations and the rotation speed of the second encoder 27 at the puncture, and instructs the driver 45 to rotate the second motor 25.

Then, initially the second motor 25 rotates in the positive direction, whereby the frame 23 moves forward at a high speed (0.05 sec) by a small distance (10 mm). Immediately thereafter, the second motor 25 is rotated in the reverse direction to move the frame 23 backward at the same speed by the same distance. The number of rotations and the rotation speed at this time are detected by the second sensor 28. The control unit 41 controls the second motor 25 so that the values obtained by the second sensor 28 become equal to the number of rotations and the rotation speed which are stored in the memory 44. When the reciprocation means 32 is moved forward, the tip of the needle 16 protrudes slightly from the puncture needle port 30a of the casing 30 through the reciprocation means 32.

As described above, when collecting blood from the patient, since protrusion of the needle 16 is carried out speedily by a small distance, physical and mental pains to the patient can be reduced.

The collected blood is subjected to measurement of blood glucose level by the blood glucose level measurement device 130 according to the fourth embodiment to be described later. The data of the measured blood glucose level is transmitted from the transmission unit 140. The transmitted data of the blood glucose level is received by the reception unit 50 of the injection device with puncture function 180 and stored in the memory 44. At this time, a required dose of insulin 12 according to the blood glucose level is calculated and displayed on the display unit 47.

Next, prior to administration of the insulin 12 to the patient, the air releasing button 38 is pressed to release the air in the cartridge 11 and the needle 16. At this time, if the touch sensor 49 does not touch the skin of the patient, the instruction unit 36 informs the control unit 41 that the air releasing button 38 is pressed. The control unit 41 obtains, from the memory 44, the number of rotations and the rotation speed of the second encoder 27 during the air releasing, and instructs the driver 45 to rotate the second motor 25. Then, the second motor 25 is initially rotated in the positive direction, whereby the reciprocation means 32 is moved forward at a low speed (0.2 sec) by a long distance (20 mm). Subsequently, the instruction unit 36 obtains, from the memory 44, the number of rotations and the rotation speed of the first encoder 19, and instructs the driver 42 to rotate the first motor 17. Then, the first motor 17 is rotated in the positive direction, whereby the extrusion means 24 is moved forward at a low speed (5 sec) by a short distance (1 mm). Thus, air releasing is automatically carried out.

The number of rotations and the rotation speed at this time are detected by the first sensor 20. The control unit 40 performs control so that the values detected by the first sensor 20 become equal to the number of rotations and the rotation speed stored in the memory 44.

Next, the instruction unit 36 informs the control unit 41 that the air releasing is ended. The control unit 41 obtains, from the memory 44, the number of rotations and the rotation speed of the second encoder 27 at the end of the air releasing, and instructs the driver 45 to rotate the second motor 25. Then, the second motor 25 is rotated in the reverse direction, whereby the reciprocation means 32 is moved backward at a low speed (0.2 sec) by a long distance (20 mm). The number of rotations and the rotation speed at this time are detected by the second sensor 28. The control unit 41 performs control so that the values detected by the second sensor 28 become equal to the number of rotations and the rotation speed stored in the memory 44.

As described above, since air releasing is automatically carried out prior to administration of the insulin 12, no air is injected into the patient, thereby ensuring safety.

Next, the administration button 39 is pressed to administer the insulin 12 to the patient. At this time, when the touch sensor 49 touches the skin of the patient, the instruction unit 36 informs the control unit 41 that the administration button 39 is pressed. The control unit 41 obtains, from the memory 44, the number of rotations and the rotation speed of the second encoder 27 during the administration, and instructs the driver 45 to rotate the second motor 25.

Then, the second motor 25 is initially rotated in the positive direction, whereby the reciprocation means 32 is moved forward at a low speed (0.2 sec) by a large distance (15 mm). Subsequently, the instruction unit 36 obtains, from the memory 44, the number of rotations and the rotation speed of the first encoder 19 during the administration, and instructs the driver 42 to rotate the first motor 17.

Then, the first motor 17 rotates in the positive direction to move the extrusion means 24 forward at a low speed (5 sec) by a distance equivalent to a set dose, and the insulin 12 is administered to the patient. The number of rotations and the rotation speed at this time are detected by the sensor 20. The control unit 40 performs control so that the values detected by the first sensor 20 become equal to the number of rotations and the rotation number which correspond to the dose of the insulin 12 which is stored in the memory 44.

As for the dose of the insulin 12, the data of blood glucose level that is transmitted from the transmission unit 140 of the measurement device 130 according to the fourth embodiment to be described later is received by the reception unit 50, and the data is stored in the memory 44. Alternatively, the dose of the insulin 12 is set by the setting button 48 and stored in the memory 44.

Next, the patient waits for five seconds in this state until the insulin 12 is completely administered into the patient. The reason why the patient should wait for five seconds is because all the insulin 12 completely flows out within this five seconds and thereby administration is surely performed. After this five seconds, the instruction unit 36 informs the control unit 41 that administration of the insulin 12 is ended. The control unit 41 obtains, from the memory 4, the number of rotations and the rotation speed of the encoder 27 at the end of the administration, ad instructs the driver 45 to rotate the second motor 25. Then, the second motor 25 rotates in the reverse direction, whereby the reciprocation means 32 moves backward at a low speed (0.2 sec) by a large distance (15 mm). The number of rotations and the rotation speed at this time are detected by the second sensor 28. The control unit 41 performs control so that the values detected by the sensor 28 become equal to the number of rotations and the rotation speed that are stored in the memory 44.

In this way, the amount of the insulin 12 received by the reception unit 50 or the amount of the insulin 12 set by the setting button 48 can be correctly administered.

As described above, the injection device with puncture function 180 according to the first embodiment includes, in the same casing 30, the function of the puncture unit for collecting blood and the function of the injection unit for administering the insulin 12, thereby realizing an injection device with puncture function that can be easily taken along.

Further, the needle 16 for collecting blood and the reciprocation means 32 for reciprocating the needle 16 are shared by collection of blood and administration of insulin 12, whereby the device is miniaturized.

Further, the extrusion means 24 includes the motor 17, the first rpm/linear motion conversion unit 43 which is provided between the rotation axis of the motor 17 and the piston 200 and converts the rpm of the first motor 17 into linear motion, and the first rpm detection unit 21 for detecting the rpm of the first motor 17, whereby administration of a correct dose of insulin 12 can be carried out with stability.

The first rpm/linear motion conversion unit 43 is constituted by the first shaft 18 having the external thread 18a at its surface, and the first nut 21 having the internal thread 21a that fits the external thread 18a, whereby the amount of movement can be precisely controlled, and further, the dose of insulin 12 can be precisely controlled.

Furthermore, the first rpm detection unit 21 is constituted by the first encoder 19 that is connected to the rotation axis of the first motor 17, and the first sensor 20 for detecting the rpm of the first encoder 19, whereby accurate rpm can be detected.

Further, the reciprocation means 32 includes the second motor 25, the second rpm/linear motion conversion unit 46 that is connected between the rotation axis of the second motor 25 and the frame 23, and the second rpm detection unit 28 for detecting the rpm of the second motor 25, whereby the amount of movement by the reciprocation means 32 can be precisely controlled, and further, the amount of movement for reciprocating the entire frame 23 can be precisely controlled.

Furthermore, the second rpm/linear motion conversion unit 46 is constituted by the shaft 26 having the external thread 26a at its surface, and the second nut 29 having the internal thread 29a that fits the external thread 26a, whereby the amount of movement by the second rpm/linear motion conversion unit 46 can be precisely controlled.

Furthermore, the second rpm detection unit 28 is constituted by the second encoder 27 that is connected to the rotation axis of the second motor 25, and the second sensor 28 for detecting the rpm of the second encoder 27, whereby accurate rpm can be detected.

The needle 16 is a hollow needle comprising metal, and the single needle 16 serves both as a puncture needle for collecting blood and as an injection needle for administrating insulin 12. Therefore, it is not necessary to provide plural needles for the respective purposes, resulting in miniaturization and cost reduction. Of course, different needles may be used for blood correction and insulin administration, respectively.

The reciprocation means 32 is moved at a high speed by a small distance during puncture while it is moved at a low speed by a large distance during extrusion of insulin 12, whereby the single reciprocation means 32 can be shared by the puncture unit and the injection unit. Therefore, it is not necessary to provide the puncture unit and the injection unit with the respective reciprocation means 32, resulting in miniaturization and cost reduction.

Next, a description will be given of a method for operating the injection device with puncture function 180, with reference to FIG. 4.

Figure 4:
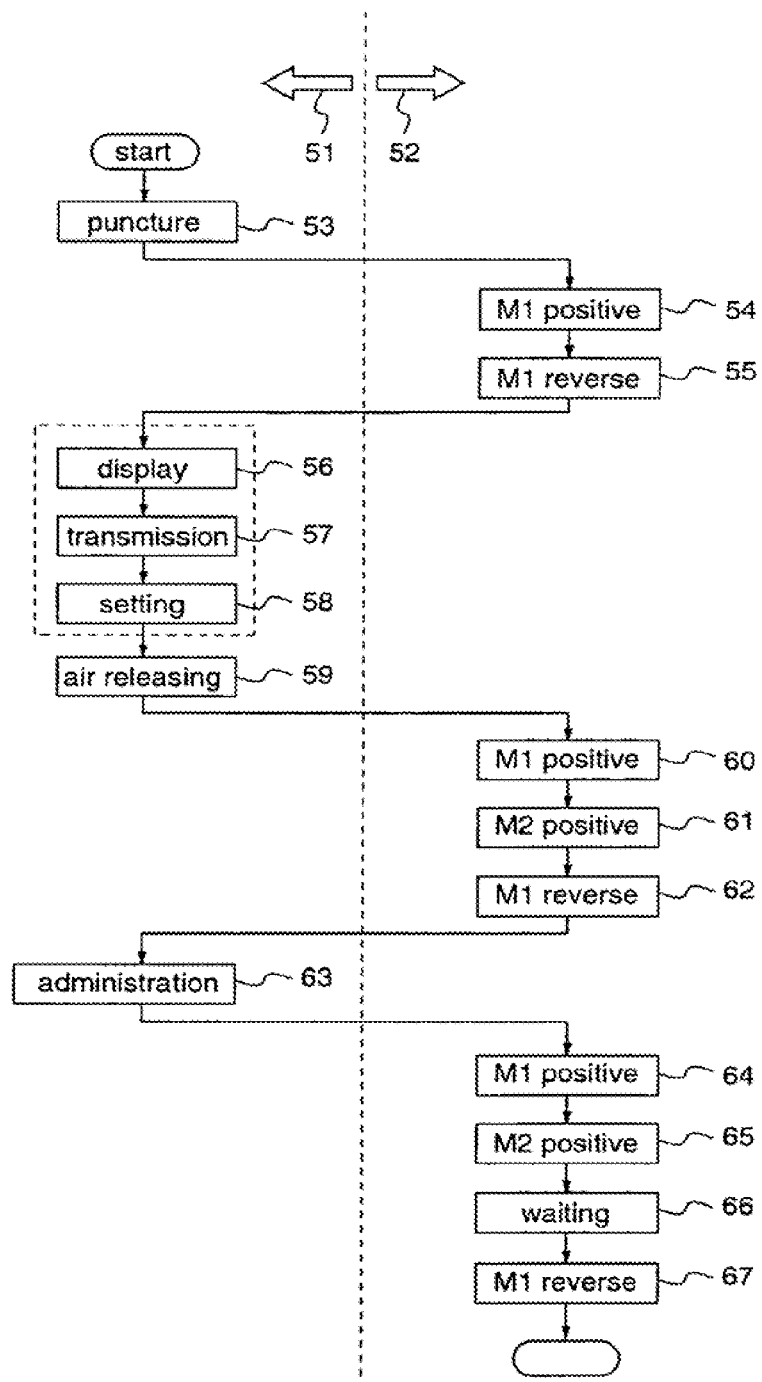
FIG. 4 is a flowchart for explaining the operation of the injection device with puncture function according to the first embodiment.

In FIG. 4, operations on the arrow 51 side relate to the patient, and operations on the arrow 52 side relate to the injection device with puncture function 135.

Initially, the patient applies the puncture needle port 30a to his/her finger tip or the like, and presses the puncture button 37 of the injection device with puncture function 180 (step 53). Then, the reciprocation means 32 moves forward at a high speed by a small distance (step 54). The needle 16 slightly protrudes from the puncture needle port 30a and punctures the finger. Immediately after the puncture, the reciprocation means 32 moves back to the original position at a high speed (step 55).

The patient collects a small amount of blood from the wounded finger, and applies the collected blood onto the sensor 111 that is attached to the measurement device 130 according to the fourth embodiment to be described later. The blood glucose level of the applied blood is measured and displayed on a display unit 138 of the measurement device 130 (step 56). The displayed blood glucose level is transmitted from a transmission part 140 of the measurement device 130 (step 57), and received by the reception unit 50 of the injection device with puncture function 180 to be stored in the memory 44. At this time, a necessary dose of insulin 12 according to the blood glucose level is calculated and displayed on the display unit 47.

The dose of insulin 12 to be administered may be adjusted by using the setting button 48 on the basis of the displayed dose of insulin 12 (step 58).

Next, in order to perform air releasing, the patient presses the air releasing button 38 (step 59). Then, the reciprocation means 32 moves forward at a low speed by a large distance (step 60). Subsequently, the extrusion means 24 moves forward (step 61), whereby the air in the cartridge 11 and the needle 16 is discharged. After a time required for completely discharging the air has passed, the reciprocation means 32 moves back to the original position at a low speed (step 62).

Next, the patient applies the puncture needle port 30a of the injection device with puncture function 180 to his/her skin, and presses the administration button 39 (step 63). Then, the reciprocation means 32 moves forward at a low speed by a large distance (step 64). Subsequently, the extrusion means 24 moves forward at a low speed (step 65), and a set dose of insulin 12 in the cartridge 11 is administered from the needle 16 to the patient. The patient waits for five seconds until the insulin 12 is completely administered and stabilized (step 66), and thereafter, the reciprocation means 32 moves at a low speed back to the original position (step 67).

Since the injection device with puncture function 180 has the air releasing steps 59~62 as described above, there is no fear that air or the like is injected into the patient by mistake, thereby ensuring safety.

The injection device with puncture function 180 according to the first embodiment includes, in the same casing, the cartridge 11 with the needle 16 being inserted at its front end and the chemical solution being enclosed therein; the cartridge holder 14 into which the cartridge 11 is inserted; the reciprocation means 32 for reciprocating the cartridge 11 and the cartridge holder 14; the extrusion means 24 for extruding the chemical solution from the rear end of the cartridge 11 toward the needle 16; and the cartridge 11 is reciprocated by the reciprocation means 32. At this time, the speed and amount of movement of the reciprocation means 32 are made variable, and puncture by the needle or administration of the chemical solution through the needle are carried out. Therefore, the injection device 180 has the function of the puncture unit for collecting blood and the function of the injection unit for administrating the chemical blood in the same casing, thereby providing an injection device with puncture function which can be easily taken along.

Embodiment 2

Figure 5:
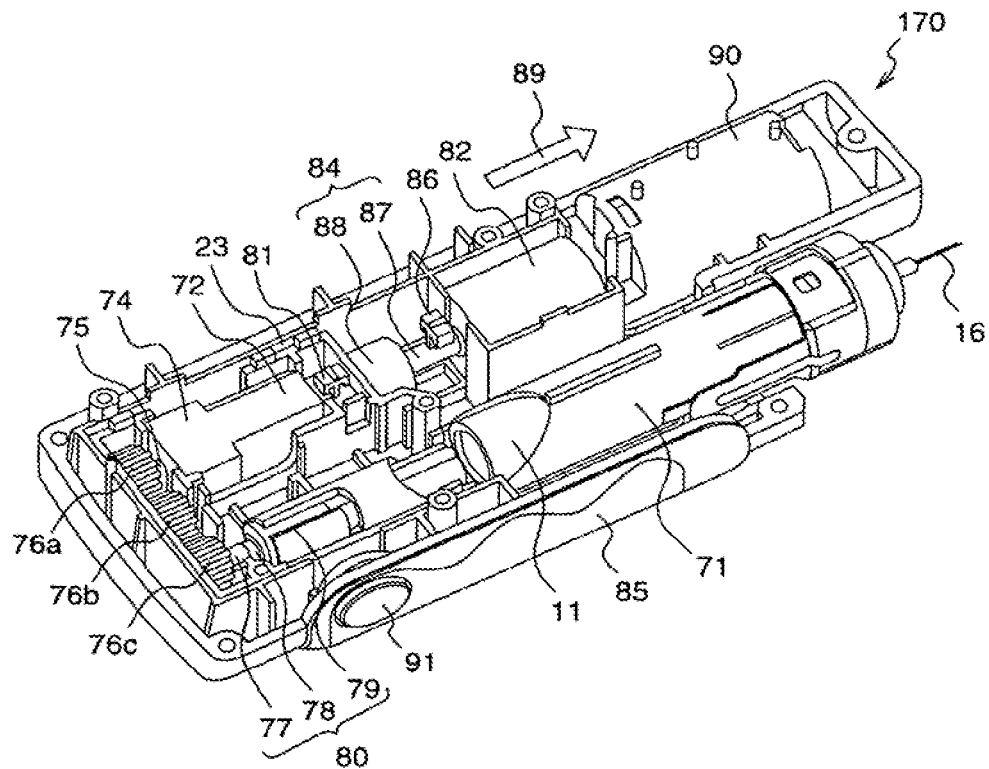
FIG. 5 is an exploded perspective view of an injection device with puncture function according to a second embodiment of the present invention.

FIG. 5 is a perspective view illustrating an injection device with puncture function 170 according to a second embodiment of the present invention, with its upper cover being opened. In FIG. 5, the same reference numerals as those used for the first embodiment denote the same elements, and therefore, repeated description is not necessary.

With reference to FIG. 5, reference numeral 11 denotes a cartridge in which insulin 12 is enclosed, and this cartridge 11 is inserted into a cartridge holder 71. Further, reference numeral 16 denotes a needle inserted at a front end of the cartridge 11.

Reference numeral 72 denotes a first motor as a component of an extrusion means 73. Rotation of the first motor 72 is transmitted to a main axis 75 through a deceleration gear 74. The main axis 75 is connected to a first shaft 77 through transmission gears 76a, 76b, 76c. The first shaft 77 is connected to a first nut 79 through an elastic extension member 78. Further, the first nut 79 is fixed in conjunction with the cartridge holder 71. The first shaft 77, the elastic extension member 78, and the first nut 79 constitute a first rpm/linear motion conversion unit 80.

Reference numeral 81 denotes a first sensor which is a first rpm detection unit for measuring the rpm of the first motor 72.

The first motor 72, the first rpm/linear motion conversion unit 80, and the first sensor 81 constitute an extrusion means 73 for extruding the chemical solution from the rear end of the cartridge 11 toward the needle 16.

Figure 6:
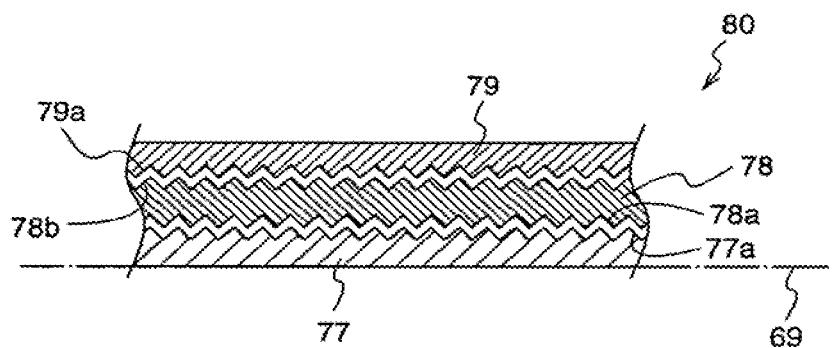
FIG. 6 is a cross-sectional view of a main part of the injection device with puncture function according to the second embodiment.

FIG. 6 is a cross-sectional view of a main part of the first rpm/linear motion conversion unit 80 according to the second embodiment.

With reference to FIG. 6, an external thread 77a is formed at the surface of the first shaft 77. An internal thread 78a that fits the external thread 77a is provided inside the elastic extension member 78, and an external thread 78b is provided at the outer side (surface side) of the elastic extension member 78. An internal thread 79a that fits the external thread 78b is provided inside the first nut 79. Reference numeral 69 denotes a center line of the first shaft 77.

As described above, since the elastic extension member 78 is disposed between the first shaft 77 and the cartridge holder 71, the amount of extrusion of the cartridge 11 can be increased while reducing the length of the injection device with puncture function 170, and furthermore, miniaturization can also be achieved. Further, since the first motor 72, the gears 76a, 76b, and 76c, and the first rpm/linear motion conversion unit 80 are arranged in a horseshoe shape, the size of the device in the longitudinal direction can be reduced, resulting in a conveniently portable device.

Reference numeral 82 denotes a second motor as a component of a reciprocation means 83. The second motor 82 is fixed to a casing 85. Reference numeral 86 denotes a second sensor which is a second rpm detection unit for measuring the rpm of a second shaft 87 connected to the second motor 82. Reference numeral 88 denotes a second nut, and an internal thread 88a is formed inside the second nut 88.

An external thread 87a that fits the internal thread 88a is formed at the surface of the second shaft 87, and the second shaft 87 and the second nut 88 constitute a second rpm to straight motion conversion unit 84.

The nut 88 is connected to a frame 23 that is equipped with the extrusion means 73 including the first motor 72. Accordingly, when the second motor 82 constituting the reciprocation means 83 is positively rotated, the frame 23 equipped with the extrusion means 73 including the first motor 72 moves in the direction of an arrow 89, and the needle 16 moves in the same direction, in conjunction with the movement of the frame 23. When the second motor 82 is reversely rotated, the frame 23 equipped with the extrusion means 73 including the first motor 72 moves in the direction opposite to the arrow 89, and the needle 16 moves back into the casing 85 in conjunction with the movement of the frame 23.

Reference numeral 90 denotes a battery serving as a power source for driving the first and second motors 72 and 82 and the like. Reference numeral 91 denotes an administration button for the insulin 12. That is, by pressing the administration button 91, the second motor 82 is positively rotated, and the frame 23 equipped with the extrusion means 73 including the first motor 72 is moved in the direction of the arrow 89, and thereafter, the first motor 72 is positively rotated, whereby the insulin 12 in the cartridge 11 is administered to the patient from the needle 16.

Figure 7:
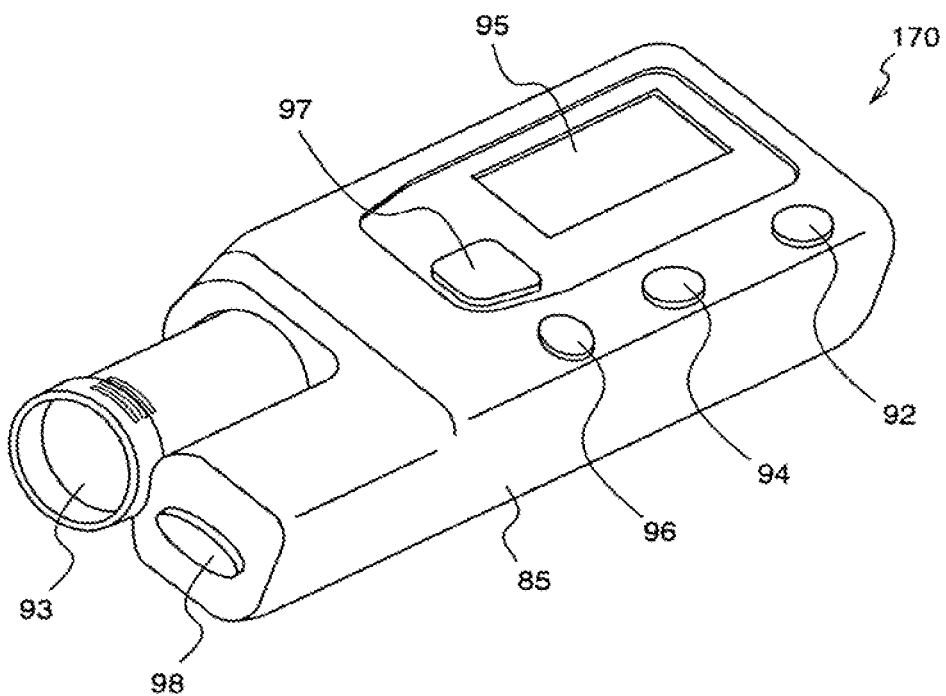
FIG. 7 is an external perspective view of the injection device with puncture function according to the second embodiment.

FIG. 7 is an external perspective view of the injection device with puncture function 170 according to the second embodiment. In FIG. 7, reference numeral 92 denotes a puncture button. When the puncture button 92 is pressed, the needle 16 protrudes from the puncture needle port 93, whereby puncture or administration of insulin 12 is carried out. Reference numeral 94 denotes a setting button, and the amount of the insulin 12 to be administered is set using the setting button 94. The set value is displayed on a display unit 95.

Also in this second embodiment, as in the first embodiment, data of measured blood glucose level is transmitted from the blood glucose level measurement device 130. Accordingly, the setting button 94 is used only when setting different from the transmitted data is desired.

Reference numeral 96 denotes an air releasing button, and the air in the cartridge 11 and the needle 16 can be removed by pressing the air releasing button 96. Reference numeral 97 denotes a power supply switch which is provided in approximately the center of the casing 85 and next to the display unit 95. Since the respective buttons are arranged in the positions mentioned above, it is avoided that the power supply is turned off by mistake during the operation.

Reference numeral 98 denotes a touch sensor which is disposed next to the puncture needle port 93. Accordingly, when performing puncture or administration of insulin 12, since the touch sensor 98 spontaneously touches the skin of the patient to sense the skin, the burden of operation can be reduced. Further, when performing air releasing, since the touch sensor 98 is spontaneously separated from the skin, it does not sense the skin, thereby ensuring safety.

As described above, in the injection device with puncture function 170 according to the second embodiment, the elastic extension member 78 is inserted between the first shaft 77 and the first nut 79, it is possible to increase the amount of extrusion of the cartridge 11 while reducing the length of the injection device 170, and further, miniaturization of the device can also be achieved. Furthermore, since the first motor 72, the gears 76a, 76b, and 76c, and the first rpm/linear motion conversion unit 80 are arranged in a horseshoe shape, the size in the longitudinal direction of the injection device 170 can be reduced, resulting in a conveniently portable device.

Moreover, since the elastic extension member 78 is disposed between the first shaft 77 and the cartridge holder 71, the amount of extrusion of the cartridge 11 can be increased while reducing the length of the injection device with puncture function 170, and furthermore, miniaturization of the device can also be achieved.

Further, since the respective buttons are arranged in the above-mentioned positions, it is prevented that the power supply is turned off by mistake during the operation.

Embodiment 3

Figure 8:
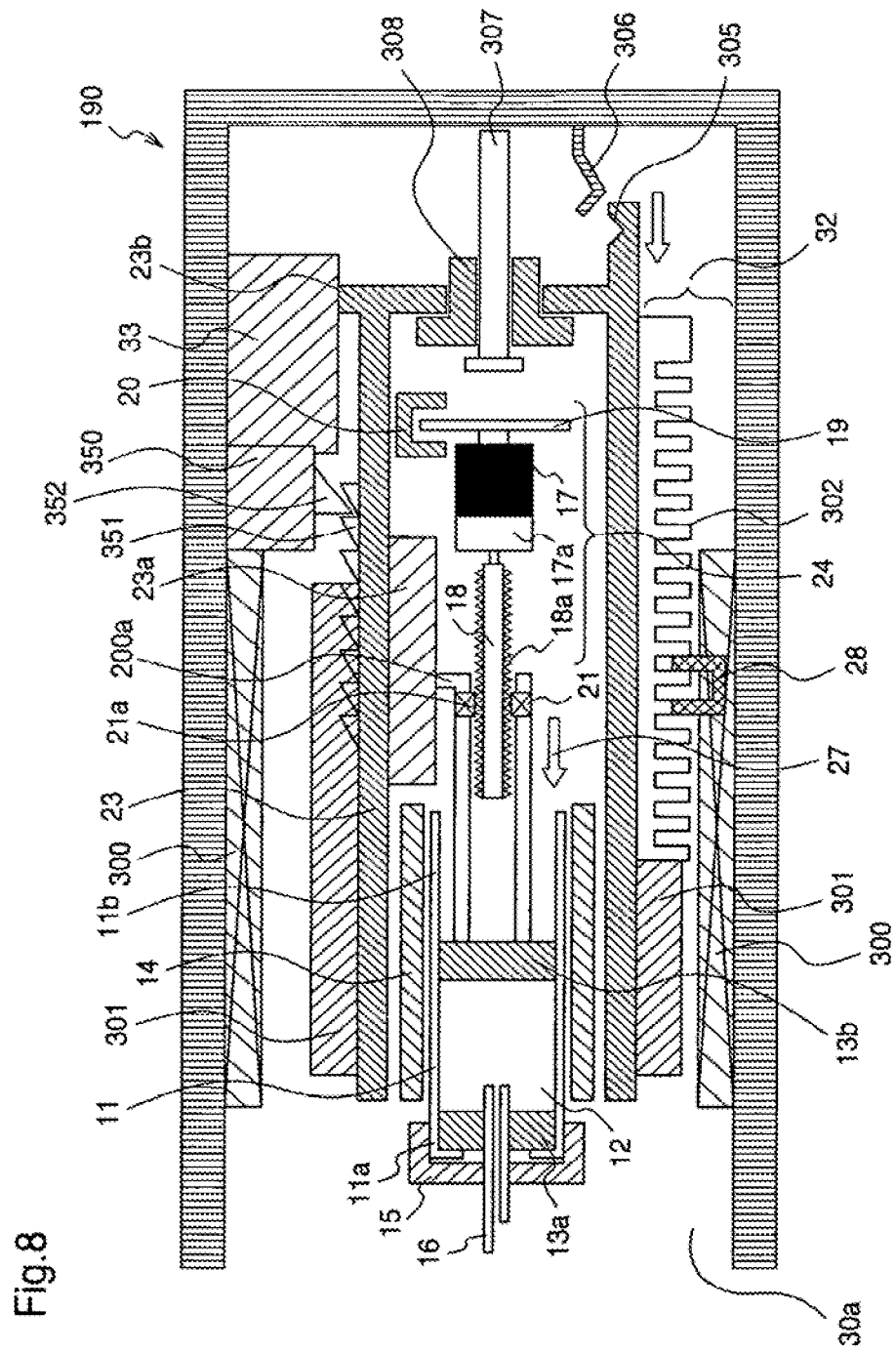
FIG. 8 is a cross-sectional view of an injection device with puncture function according to a third embodiment of the present invention.

FIG. 8 is a cross-sectional view of an injection device with puncture function 190 according to a third embodiment of the present invention.

In the first and second embodiments, the injection device with puncture function is driven by two motors, such as the first motor 17 and the second motor 25 for the injection device 180 of the first embodiment, or the first motor 72 and the second motor 82 for the injection device 170 of the second embodiment. However, the injection device with puncture function 190 according to the third embodiment is constituted such that a coil and a magnet are used instead of the second motor that is one of the two motors, and a driving force is applied to the reciprocation means by the coil and the magnet.

The puncture and blood-collecting operation of injection device with puncture function 190 constituted as described above have the following characteristics.

(Characteristics of Puncture and Blood-Collecting Operation)

A coil 300 and a magnet 301 serve as a source of power for the reciprocation means that reciprocates the extrusion means 24 and the cartridge 11 including the needle 16, which are contained in the frame 23.

The magnet 301 is fixed onto the frame 23, and when a current flows in the coil 300, the entirety of the frame 23 on the magnet 301 side moves forward and backward.

A linearly arranged second encoder, i.e., a linear encoder 302, is provided, and the second sensor 28 detects the position of the second encoder 302. In this construction, pulse signals are outputted from the second encoder 302, and an absolute position of the linear motor realized by the combination of the coil 300 and the magnet 301, from H.P. (home position) that is an original point of the frame 23 can be detected by counting the pulse signals.

In the initial state before puncture is started, the first latch 306 attached to the casing 30 and the second latch 305 attached to the frame 23 are engaged with each other, whereby the injection device with puncture function 190 and the frame 23 are relatively fixed to each other to set them in the stand-by state.

When starting the puncture operation, a predetermined current is applied to the coil 300, whereby the entirety of the frame 23 is subjected to a driving power by electromagnetic power generated between the coil 300 and the magnet 301. At this time, the linear motion of the frame 23 is guided by the frame convex portion 23b and the rail 33, and the guide pin 307 and the guide push 308.

The engagement of the first latch 306 and the second latch 305 is released by the driving force.

Thereafter, an absolute position of the second encoder 302 that is integrated with the frame 23 is detected by counting the pulse signals from the second sensor 28.

When a predetermined number of pulse signals are counted, i.e., when the puncture position of the needle 16 due to the linear motion of the frame 23 is detected, the current that flows in the coil 300 is turned off.

During the puncture operation, the current that flows in the coil 300 is turned off when the puncture is completely ended, and simultaneously, the current direction is reversed to apply a force that brings the frame 23 back to the H.P.

That is, after the puncture of the needle 16, the direction of the current that flows in the coil 300 is reversed, whereby the frame 23 moves back to the initial position where the first latch 306 and the second latch 305 are engaged, whereby one puncture operation is completed.

During the puncture and blood-collecting operation, the ratchet button 350 and the ratchet claw 351 which are positioned as shown in FIG. 8 are not engaged. That is, a claw tip portion 352 of the ratchet button 350 is retracted to avoid improvident engagement of the ratchet claw tip portion 352 and the ratchet claw 351, whereby the frame 23 can be smoothly moved.

Further, the needle insertion and chemical-injecting operation of the injection device with puncture function 190 according to the third embodiment have the following characteristics.
(Characteristics of Needle Insertion and Chemical-Injecting Operation)

When injection of a chemical solution (insulin) is carried out, engagement of the ratchet tip portion 352 and the ratchet claw 315 is released, and the frame 23 is moved forward at the minimum pitch unit of the ratchet claw, thereby to perform positioning.

Further, the position can be determined by detecting, with the linear encoder 302, that a predetermined amount of puncture (amount of needle that punctures the skin) is reached.

With the predetermined degree of puncture, the current to the coil 300 is turned off. Simultaneously, since the ratchet claw tip portion 352 is projected, the ratchet tip portion 352 and the ratchet claw 351 are engaged with each other, whereby the frame 23 stops without moving back to the H.P.

In this state, the chemical solution is injected.

Thereafter, the ratchet claw tip portion 352 is retracted by an electrical means, whereby engagement of the ratchet tip portion 352 and the ratchet claw 351 is released, and further, the current that flows in the coil 300 is reversed, whereby the frame 23 is moved back to the position where the first latch 306 and the second larch 305 are engaged with each other, thereby completing the sequence of operations.

In this way, the injection device with puncture function 190 according to the third embodiment can perform the puncture and blood-collecting operation, and the needle insertion and chemical-injecting operation.

As described above, while in the first and second embodiments the injection device with puncture function is driven with two motors, in the injection device with puncture function 190 according to the third embodiment, one of the two motors, i.e., the second motor, is constituted by a coil and a magnet that give a driving force to the reciprocation means. Therefore, as in the first and second embodiments, it is possible to realize an easily portable injection device with puncture function in which the function of the puncture unit and the function of the injection unit are integrated in the same casing, and moreover, this device can be implemented by the power-saving construction.

Embodiment 4

Figure 9:
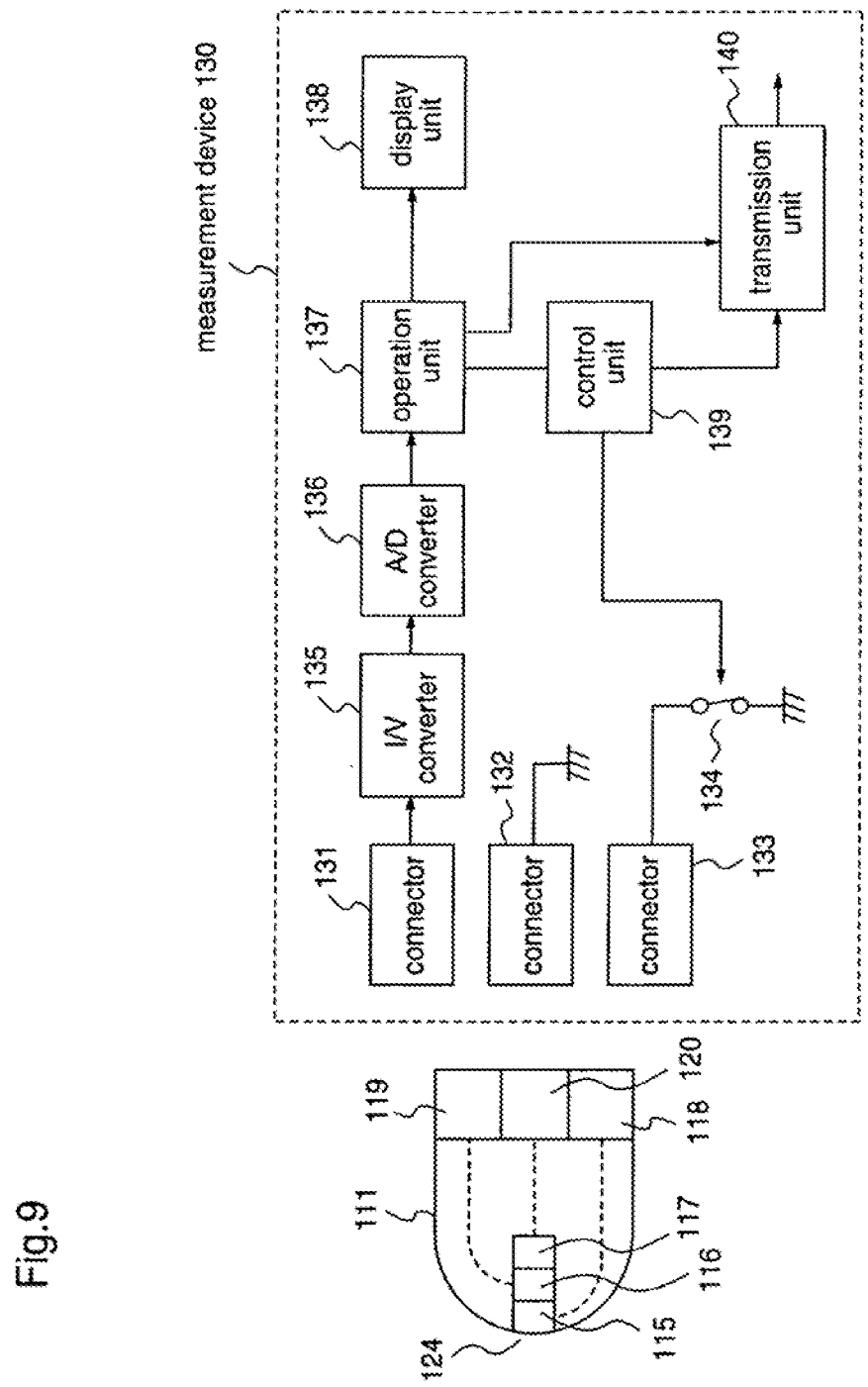
FIG. 9 is a block diagram illustrating the sensor and the measurement device according to the fourth embodiment.

FIG. 9 is a block diagram illustrating a sensor 111 and a blood glucose level measurement device 130 into which the sensor 111 is inserted, according to a fourth embodiment of the present invention.

With reference to FIG. 9, reference numeral 131 denotes a connector to which the terminal 119 is connected, and numeral 132 denotes a connector to which the terminal 120 is connected. Further, numeral 133 denotes a connector to which the terminal 118 is connected.

The connector 132 is directly connected to the ground, and the connector 133 is connected to the ground via an electronic switch 134 that is constituted by an electronic circuit. Further, the connected 131 is connected to an input of a current/voltage converter 135, and an output thereof is connected to an operation unit 137 via an analog/digital converter (hereinafter referred to as an A/D converter) 136. An output of the operation unit 137 is connected to a display unit 138 that is constituted by a liquid crystal.

Reference numeral 139 denotes a control unit, and an output of the control unit 139 is connected to a control terminal of the electronic switch 134, the operation unit 137, and a transmission unit 140. Further, the output of the operation unit 137 is also connected to an input of the transmission part 140.

Data of the blood glucose level measured by the measurement device 130 is transmitted from the transmission unit 140 to be received by the reception unit 50 of the injection device with puncture function 180, 170, or 190. The received data is stored in the memory 44. Accordingly, the measurement is carried out without intervening someone's hand, there is no trouble of setting the blood glucose level, and setting error is avoided.

Although electric wave may be used as means for transmitting the data from the transmission part 140, it is desirable to transmit the data using optical communication or cable to avoid malfunction of a medical appliance and the like.

Using the sensor and the measurement device according to the fourth embodiment, it is possible to measure blood glucose level of blood that is obtained by performing puncture with any of the injection devices with puncture function according to the first, second, and third embodiments. Accordingly, administration of chemical solution can be carried out while controlling the dose of the chemical solution on the basis of the result of the measurement.

Embodiment 5

Figure 10:
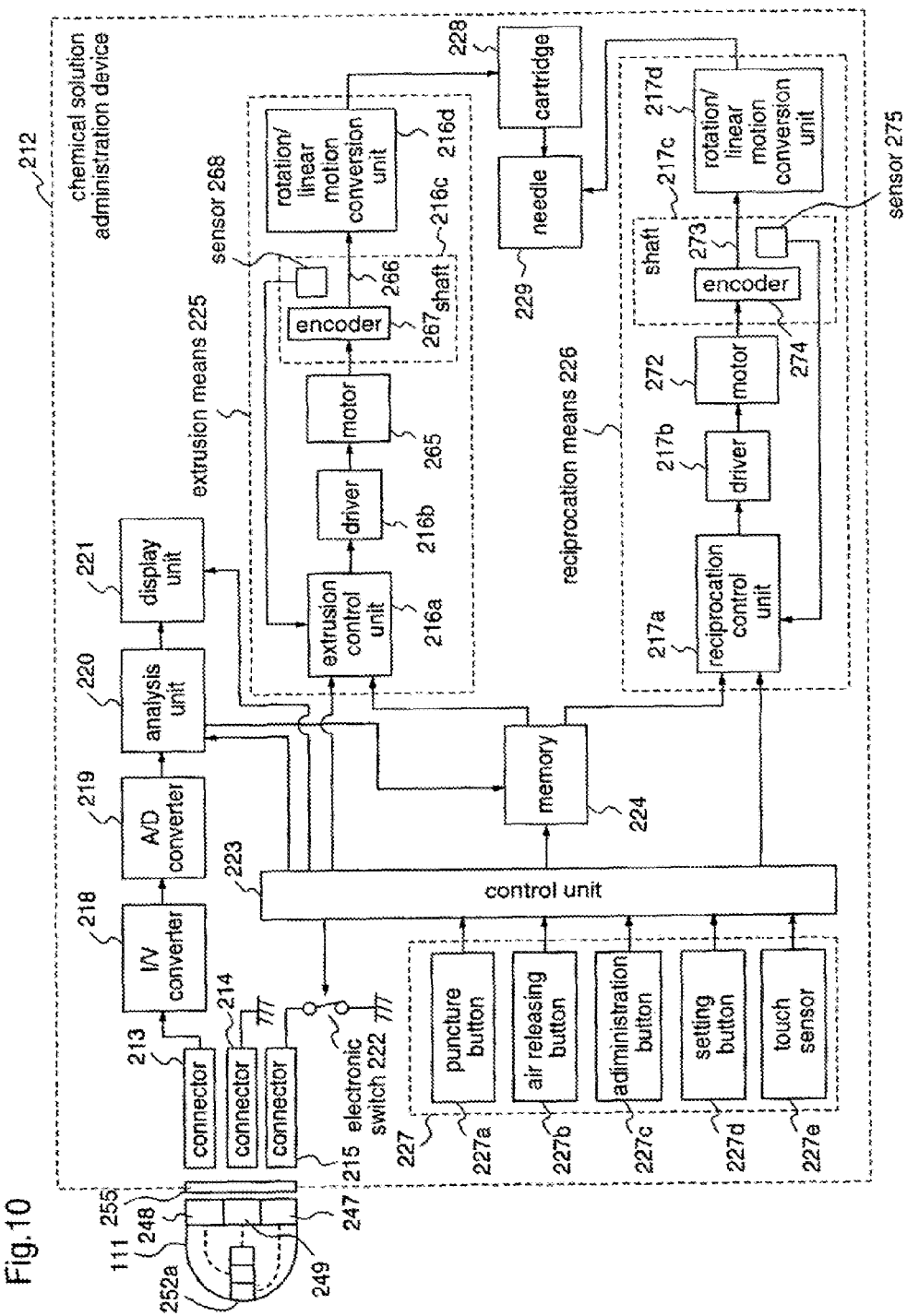
FIG. 10 is a block diagram of a chemical solution administration device according to a fifth embodiment of the present invention.

FIG. 10 is a block diagram illustrating a chemical solution administration device 212 according to a fifth embodiment of the present invention.

In FIG. 10, reference numeral 111 denotes a blood sensor, and numeral 212 denotes a chemical solution administration device to which the blood sensor 111 is connected.

An output of the blood sensor 111 is connectable to connectors 213~215. The connector 213 is connected to an input of a current/voltage converter 218. An output of the current/voltage converter 218 is connected to an input of an analysis unit 220 through an analog/digital converter (hereinafter referred to as an A/D converter) 219. An output of the analysis unit 220 is connected to a display unit 221 that is constituted by liquid crystal. The connector 214 is grounded, and the connector 215 is grounded through an electronic switch 222 that is constituted by an electronic circuit.

Reference numeral 223 denotes a controller, and an output of the controller 223 is connected to a control terminal of the electronic switch 222, the analysis unit 220, the display unit 221, a memory 224, an output of an extrusion means 225, and an output of a reciprocation means 226. An input unit 227 comprising buttons 227a~227e is connected to an input of the controller 223.

The output of the analysis unit 220 is connected to the memory 224, and an output of the memory 224 is connected to the other input of the extrusion means 225 and the other input of the reciprocation means 226. An output of the extrusion means 225 contacts an end of a cartridge 228 in which insulin that is used as an example of a chemical solution is enclosed, and the other end of the cartridge 228 is connected to a needle 229 that performs puncture, i.e., administration of insulin.

The extrusion means 225 comprises an extrusion control unit 216a to which the output of the memory 224 and the output of the controller 223 are connected, a driver 216b to which an output of the extrusion control unit 216a is connected, a first motor 265 to which an output of the driver 216b is connected, a first shaft 266 to which an output of the first motor 265 is connected, a first encoder 267 attached to the first shaft 266, a first rpm/linear motion conversion unit 216d that is connected to a piston 280 (detail will be described later with reference to FIG. 15) through the first shaft 266, and a first sensor 268 which detects the rpm of the first encoder 267, and outputs it to the extrusion control unit 216a.

The first encoder 267 and the first sensor 268 constitute a first rpm detection unit 216c.

The first rpm/linear motion conversion unit 216d comprises the first shaft 266 having an external thread at its surface, and the piston 280 which is fixed to a first nut 269 having an internal thread that fits the external thread.

An output of the reciprocation means 226 is also connected to the needle 229. The extrusion means 225 makes the insulin enclosed in the cartridge 228 flow from the needle 229 to administer the insulin to the patient. The reciprocation means 226 moves the needle 229 forward and backward.

The reciprocation means 226 comprises a reciprocation control unit 217a to which the output of the memory 224 and the output of the controller 223 are connected, a driver 217b to which an output of the reciprocation control unit 217a is connected, a second motor 272 to which an output of the driver 217b is connected, a second shaft 273 to which an output of the second motor 272 is connected, a second encoder 274 attached to the second shaft 273, a second rpm/linear motion conversion unit 217d connected to the second shaft 273, and a second sensor 275 which detects the rpm of the second encoder 274, and outputs it to the reciprocation control unit 217a. The second encoder 274 and the second sensor 275 constitute a second rpm detection unit 217c. Further, the second rpm/linear motion conversion unit 217d comprises the second shaft 273 having an external thread at its surface, and a frame 281 which is fixed to a second nut 276 having an internal thread that fits the external thread.

The input unit 227 is connected to the controller 223. The input unit 227 comprises a puncture button 227a for instructing puncture, an air releasing button 227b for instructing air releasing, an administration button 227c for instructing administration of insulin, a setting button 227d for changing or newly setting the dose of insulin 61, and a touch sensor 227e for detecting whether the puncture needle port of the chemical solution administration device 212 touches the skin of the patient or not.

Next, a description will be given of the operation of the chemical solution administration device 212 according to the fifth embodiment, with reference to FIGS. 9~13.

Figure 11:
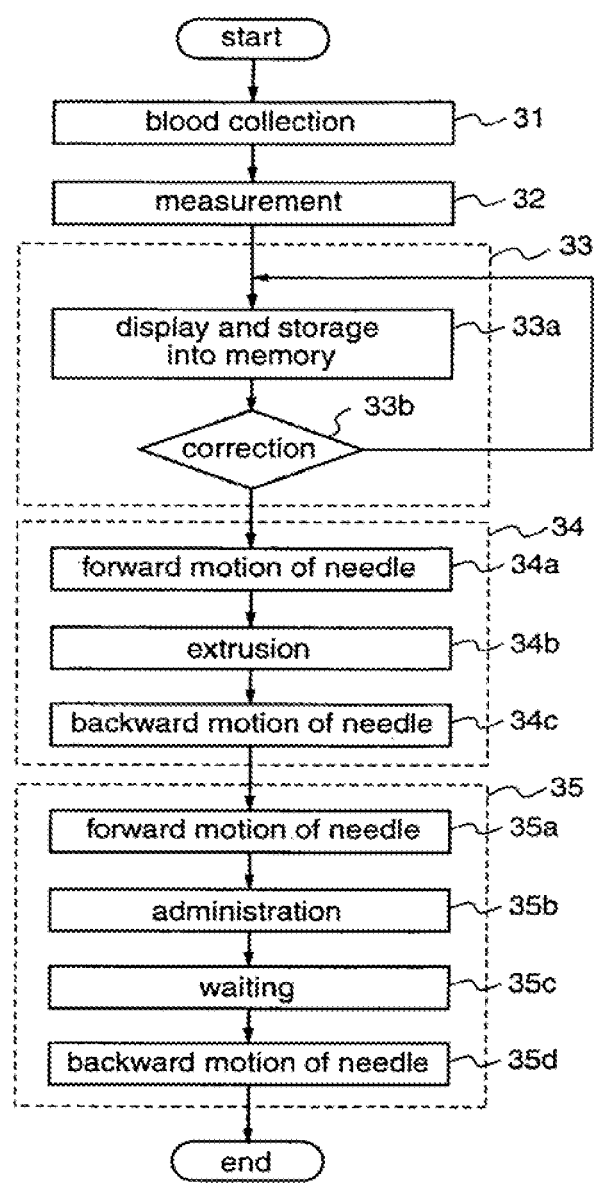
FIG. 11 is a flowchart for explaining the operation of the chemical solution administration device according to the fifth embodiment.

FIG. 11 is a flowchart for explaining the operation of the chemical solution administration device 212. With reference to FIG. 11, reference numeral 31 denotes a step of collecting blood. In the step 31, initially, the puncture button 227a is pressed to collect blood from the patient. At this time, on condition that the touch sensor 227e touches the skin of the patient, the controller 223 informs the reciprocation control unit 217a that the puncture button 227a is pressed. The reciprocation control unit 217a obtains the number of rotations and the rotation speed of the second encoder 274 at the puncture from the memory 224, and instructs the driver 217b to rotate the motor 272.

Then, the second motor 272 initially rotates in the positive direction to move the reciprocation means 226 forward at a high speed (0.05 sec) by a small distance (10 mm). Immediately thereafter, the second motor 272 is rotated reversely to move the reciprocation means 226 backward at the same speed by the same distance. The number of rotations and the rotation speed at this time are detected by the second sensor 275. The reciprocation control unit 217a performs control so that the values detected by the second sensor 275 become equal to the number of rotations and the rotation speed that are stored in the memory 224.

When the reciprocation means 226 is moved forward, the tip of the needle 229 slightly protrudes from a puncture needle port 227a of a casing 277 (detail will be described later with reference to FIG. 12).

In the blood collecting step 31, since protrusion of the needle 229 is carried out at a high speed by a small distance, physical and mental pains to the patient can be reduced.

The blood glucose level of the collected blood is measured by the chemical solution administration device 212 in step 32. Although a method for measuring the blood glucose level from blood will be described later, conclusively it is carried out as follows. Blood dropped onto a sample application port 252a of the blood sensor 111 chemically reacts with a reagent, and a reaction current at this time is detected and analyzed by the analysis unit 220, thereby to measure a blood glucose level. Further, the analysis unit 220 has a conversion function, and calculates a dose of insulin 61 to be administered, on the basis of the measured blood glucose level.

In the next step 33, data of the blood glucose level analyzed by the analysis unit 220 and the dose of insulin 61 to be administered are displayed on the display unit 221, and simultaneously, the data is transmitted by cable or radio wave to be stored in the memory 224 (step 33a).

In this fifth embodiment, cable, i.e., pattern connection on a wiring substrate, is used for the communication. Accordingly, reliability of connection is preferable.

An important point in this fifth embodiment is that the data of the blood glucose level analyzed by the analysis unit 220 and the dose of insulin 61 to be administered are automatically stored in the memory 224. Since the data of the blood glucose level is automatically stored, the operator is saved from the burden of memorizing the data and correctly setting the same with the setting button, and furthermore, incorrect setting due to inputting error is avoided, thereby realizing accurate setting.

The data of blood glucose level stored in the memory 224 and the dose of insulin 61 to be administered (which are identical to the data displayed on the display unit 221) are checked, and the data of the dose of insulin 61 which is stored in the memory 224 can be rewritten with the setting button 227d.

However, the dose of insulin 61 is limited within a variable range so that the operator cannot change the setting over the range, whereby excess and deficiency do not occur in administration of the insulin 61. At this time, since the data indicating the dose of the insulin 61, which is displayed on the display unit 221, also changes, it is possible to change the dose while checking the same on the display unit 221.

If the dose of insulin 61 is not changed, the data transmitted from the analysis unit 220 are remained in the memory 224. The dose of insulin 61 is determined according to the data written in the memory 224 (step 33b).

Next, the operation goes to step 34. In step 34, prior to administration of the insulin 61 to the patient, the air in the cartridge 228 and the needle 229 is released. In this step, the air releasing button 227b is pressed. On condition that the touch sensor 227e does no contact the skin of the patient (non-contact), the controller 223 informs the reciprocation control unit 217a that the air releasing button 227b is pressed. Initially, the reciprocation control unit 217a expose the needle 229 from the puncture needle port 277a. For this purpose, the reciprocation control unit 217a obtains, from the memory 224, the number of rotations and the rotation speed of the second encoder 274 during the air releasing, and instructs the driver 217b to rotate the second motor 272. Then, the second motor 272 initially rotates in the positive direction to move the reciprocation means 226 forward at a low speed (0.2 sec) by a large distance (15 mm) (step 34a).

Subsequently, in order to push the air out of the cartridge 228, the extrusion control unit 216a obtains, from the memory 224, the number of rotations and the rotation speed of the first encoder 267 during the air releasing, and instructs the driver 216b to rotate the first motor 265. Then, the first motor 265 rotates in the positive direction, whereby the extrusion means 225 is moved forward at a low speed (5 sec) by a small distance (1 mm). Thus, air releasing is automatically carried out. The number of rotations and the rotation speed at this time are detected by the first sensor 268. The extrusion control unit 216a performs control so that the values detected by the first sensor 268 become equal to the number of rotations and the rotation speed that are stored in the memory 224 (step 34b).

Next, in order to house the exposed needle 229 into the puncture needle port 277a, the controller 223 informs the reciprocation control unit 217a that the air releasing is completed. The reciprocation control unit 217a obtains, from the memory 224, the number of rotations and the rotation speed of the second encoder 274 at the end of the air releasing, and instructs the driver 217b to rotate the second motor 272. Then, the second motor 272 rotates in the reverse direction, whereby the reciprocation means 226 is moved backward at a low speed (0.2 sec) by a large distance (15 mm). The number of rotations and the rotation speed at this time are detected by the sensor 275. The reciprocation control unit 217a performs control so that the values detected by the sensor 275 become equal to the number of rotations and the rotation speed that are stored in the memory 224.

As described above, since air releasing is automatically carried out prior to administration of the insulin 61, it is avoided that the air is injected into the patient by mistake, thereby ensuring safety (step 34c).

Next, the operation goes to step 35. In step 35, the administration button 227c is pressed to administer the insulin 61 to the patient. On condition that the touch sensor 227 touches the skin of the patient, the controller 223 informs the reciprocation control unit 217a that the administration button 227c is pressed. In order to protrude the needle 229 from the puncture needle port 277a and puncture the skin with the needle 229, the reciprocation control unit 217a obtains, from the memory 224, the number of rotations and the rotation speed of the second encoder 274 during administration, and instructs the driver 217b to rotate the second motor 272.

Then, the second motor 272 rotates in the positive direction, whereby the reciprocation means 226 is moved forward at a low speed (0.2 sec) by a large distance (15 mm) (step 35a).

Subsequently, in order to administer the insulin 61 to the patient, the extrusion control unit 216a obtains, from the memory 224, the number of rotations and the rotation speed of the first encoder 267 during administration, and instructs the driver 216b to rotate the first motor 265.

Then, the first motor 265 rotates in the positive direction, whereby the extrusion means 225 is moved forward at a low speed (5 sec) by a distance equivalent to the set dose, and the insulin 61 is administered to the patient. The amount of the forward movement of the extrusion means 225 is a value that is set by the analysis unit 220 or the setting button 227d, and it is stored in the memory 224. The number of rotations and the rotation speed at this time are detected by the first sensor 268. The extrusion control unit 216a performs control so that the values detected by the first sensor 268 become equal to the number of rotations and the rotation speed which correspond to the dose of the insulin 61 that is stored in the memory 224 (step 35b).

Next, in the state where the forward movement of the extrusion means 225 is completed, the patient holds the state for five seconds until the insulin 61 is completely administered to the patient. The reason why the patient should wait for five seconds is because the insulin 61 completely flows out during this five seconds and thereby administration is reliably performed (step 35c).

When the waiting time of five seconds has passed, in order to house the needle 229 into the puncture needle port 277a, the controller 223 informs the reciprocation control unit 217a that administration of the insulin 61 is ended. The reciprocation control means 217a obtains, from the memory 224, the number of rotations and the rotation speed of the second encoder 274 at the end of administration, and instructs the driver 217b to rotate the second motor 272.

Then, the second motor 272 rotates in the reverse direction, whereby the reciprocation means 226 is moved backward at a low speed (0.2 sec) by a large distance (15 mm). The number of rotations and the rotation speed at this time are detected by the second sensor 275. The reciprocation control unit 217a performs control so that the values detected by the second sensor 175 become equal to the number of rotations and the rotation speed that are stored in the memory 224 (step 35d).

The chemical solution administration device 212 according to the fifth embodiment has, in the same casing 277, the function of the puncture device for collecting blood, the function of the measurement device for measuring the blood glucose level of the collected blood, and the function of the injection device for administrating a dose of insulin on the basis of the data obtained by the measurement device. Therefore, the dose of insulin is automatically set, and human-inducible mistake is eliminated in the setting method, whereby the operator is saved from troublesome setting as well as from worrying about setting of an accurate dose of insulin.

Since these three functions are integrated in the same casing 277, it is possible to realize a chemical solution administration device that can be easily taken along.

Since the needle 229 for collecting blood and the reciprocation means 226 for reciprocating the needle 229 are shared between collection of blood and administration of insulin 61, further reduction in size of the device can be achieved. Of course, different needles may be used for collection of blood and administration of insulin 61, respectively.

Since the extrusion means 225 includes the first rpm/linear motion conversion unit 216d for converting the rpm of the first motor 265 to linear motion, and the first rpm detection unit 216c for detecting the rpm of the first motor 265, an accurate dose of insulin 61 can be administered with stability.

Further, since the first rpm/linear motion conversion unit 216d comprises the first shaft 266 having the external thread at its surface, and the first nut 269 having an internal thread that fits the external thread (detail will be described with reference to FIG. 12), the amount of movement can be precisely controlled, and the dose of insulin 61 can be precisely controlled.

Since the first rpm detection unit 216c comprises the first encoder 267 connected to the rotation axis of the first motor 265, and the first sensor 268 for detecting the rpm of the first encoder 267, it can detect precise rpm.

Since the reciprocation means 226 comprises the second motor 272, the second rpm/linear motion conversion unit 217d connected to the rotation axis of the motor 272 and to the rear end of the extrusion means 225, and the second rpm detection unit 217c for detecting the rpm of the second motor 272, it can precisely control the amount of movement.

Since the second rpm/linear motion conversion unit 217d comprises the second shaft 273 having the external thread at its surface, and the second nut 276 having an internal thread that fits the external thread, it can precisely control the amount of movement.

Since the second rpm detection unit 217c comprises the second encoder 274 connected to the rotation axis of the second motor 272, and the second sensor 275 for detecting the rpm of the second encoder 274, it can detect precise rpm.

The needle 229 is a hollow needle comprising metal, and the single needle 229 serves both as a puncture needle for collecting blood and as an injection needle for administering insulin 61. Therefore, it is not necessary to provide needles for blood collection and administration, respectively, resulting in miniaturization and cost reduction.

The reciprocation means 226 is moved at a high speed by a small distance during puncture, while it is moved at a low speed by a large distance when extruding the insulin 61. Accordingly, since the single reciprocation means 226 can be shared between the puncture function and the injection function, it is not necessary to provide reciprocation means for the respective functions, thereby achieving miniaturization and cost reduction.

Figure 19:
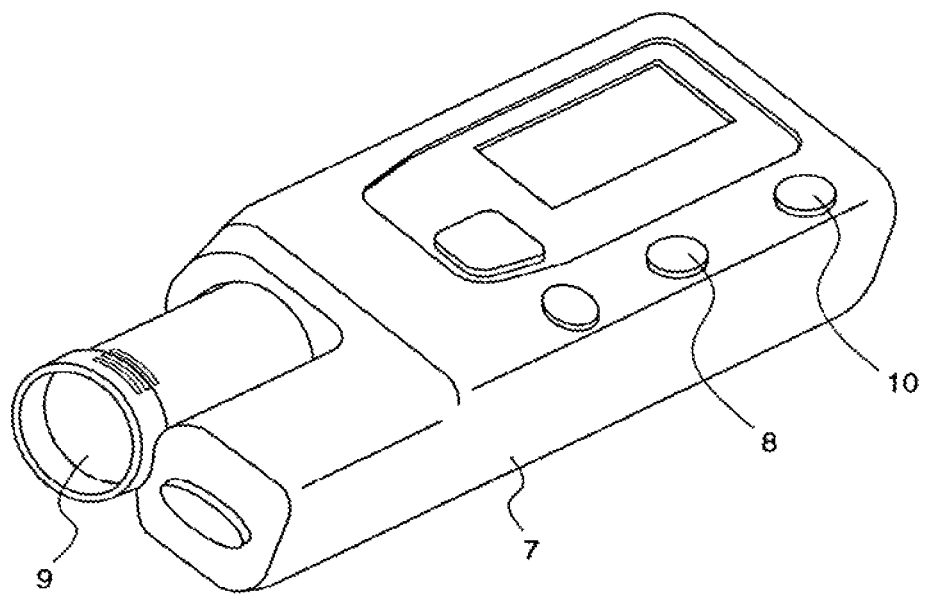
FIG. 19 is an external perspective view of a conventional injection device.

Then constructions of the sensor 111 to which blood is applied and the measurement device 130 using the sensor 130 in the chemical solution administration device 212 according to the fifth embodiment are identical to those of the fourth embodiment shown in FIG. 19, and the measurement principle thereof is also identical to that described for the fourth embodiment.

Next, a description will be given of the operations of the chemical solution administration device 212 and the blood sensor 111 according to the fifth embodiment, with reference to FIGS. 10~13.

Initially, as an initial state, the electronic switch 222 is turned off with a signal outputted from the control unit 223.

Next, the blood sensor 111 is inserted into an insertion port 255 of the chemical solution administration device 212. That is, the terminals 119, 120, and 118 of the blood sensor 111 are connected to the connectors 213, 214, and 215 of the chemical solution administration device 212, respectively.

Since the electronic switch 222 is off in this state, the counter electrode 115 and the ground are in the non-contact state. A constant voltage is supplied from the current/voltage converter 218 to the space between the measurement electrode 116 and the detection electrode 117.

Next, blood is dropped onto the inlet port 124 of the blood sensor 111. Then, the blood is aspirated by capillary phenomenon, and flows on the counter electrode 115 and the measurement electrode 116 to reach the detection electrode 117. At this time, an electric change occurs between the measurement electrode 116 and the detection electrode 117.

This electric change is converted into a voltage change by the current/voltage converter 218 through the terminal 248 and the connector 213. The output of the current/voltage converter 218 is converted into a digital quantity by the A/D converter 219, and the analysis unit 220 recognizes from the converted value that measurable blood is supplied between the measurement electrode 116 and the detection electrode 117. To be specific, a measurable amount of blood is supplied to the blood sensor 111, and thus measurement of blood glucose level can be started.

Then, the control unit 223 turns on the electronic switch 222 to connect the counter electrode 115 to the ground. During a predetermined period of time after the turn-on of the electronic switch 222, the control unit 223 performs control so that no voltage is supplied from the current/voltage converter 218 to the measurement electrode 116. During this period of time, reaction of the blood with the reagent layer 121 disposed on the counter electrode 115, the measurement electrode 116, and the detection electrode 117 is advanced. After a predetermined period of time, about 5 seconds, has passed, a predetermined voltage is supplied from the current/voltage converter 218 to the space between the measurement electrode 116 and the counter electrode 115 and to the space between the measurement electrode 116 and the detection electrode 117. At this time, current in proportion to the glucose concentration in the blood is generated between the measurement electrode 116 and the counter electrode 115 and between the measurement electrode 116 and the detection electrode 117.

This current is converted into a voltage by the current/voltage converter 218, and the voltage is converted into a digital value by the A/D converter 219. Then, the converted digital data is captured in the analysis unit 220. The analysis unit 220 calculates a blood glucose level from the digital value, and calculates a dose of insulin 61 to be administered from the calculated blood glucose level. The calculated dose is displayed on the display unit 221, and stored in the memory 224.

While measurement of glucose has been described above, the blood sensor 111 and the chemical solution administration device 212 according to the fifth embodiment are also applicable to measurement of blood components such as lactate or cholesterol.

Figure 12:
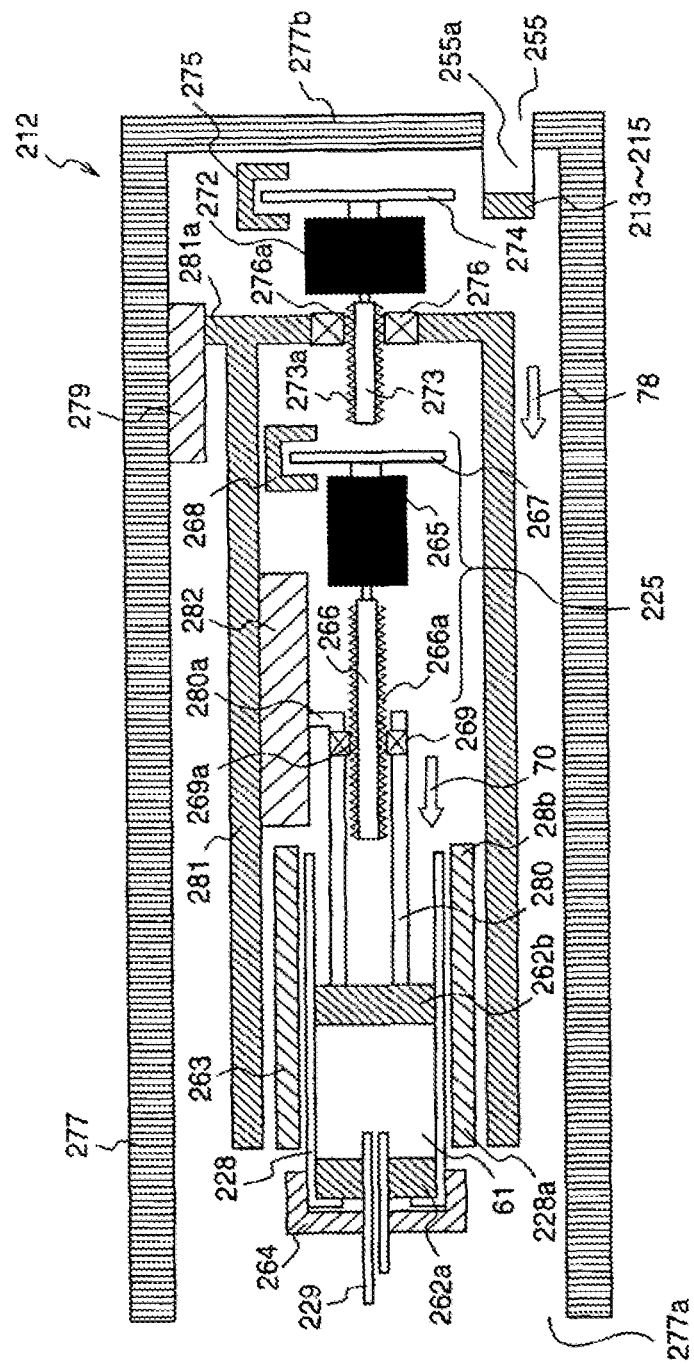
FIG. 12 is a cross-sectional view of the chemical solution administration device according to the fifth embodiment.

FIG. 12 is a cross-sectional view of the chemical solution administration device 212 according to the fifth embodiment of the present invention.

With reference to FIG. 12, reference numeral 228 denotes a cylindrical cartridge in which insulin 61 adopted as an example of a chemical solution is enclosed, and rubber stoppers 262a and 262b are inserted at a front end 228a and a rear end 228b of the cartridge 228, respectively.

Reference numeral 263 denotes a cartridge holder into which the cartridge 228 is inserted, and the cartridge 228 is attached to the cartridge holder 263. A circular cap 264 is attached to the front end of the cartridge 228. A hollow needle 229 comprising metal is attached in approximately the center of the cap 264. A root side of the needle 264 penetrates the stopper 262a that is inserted at the front end 228a of the cartridge 228 to reach the insulin 61.

Reference numeral 265 denotes a DC (direct current) motor that is used as a power for extruding the insulin 61 toward the needle 229. The rotation axis of this motor 265 is connected to a first shaft 266 through a deceleration mechanism (not shown) comprising a gear. An external thread 266a is formed at the surface of the first shaft 266.

Reference numeral 267 denotes an encoder provided in conjunction with the output axis of the first motor 265, and numeral 268 denotes a transmissive sensor for detecting rotation (rotation amount and rotation speed) of the encoder 267. The first sensor 268 is not necessarily of a transmissive type, and it may be a reflective sensor. Further, the first encoder 267 is a circular plate in shape as shown in FIG. 5. Reference numeral 267a denotes the center of rotation of the encoder 267, and numeral 267b denotes holes that are provided on an inner concentric circle in the vicinity of an outer circumference of the encoder 267.

Figure 13:
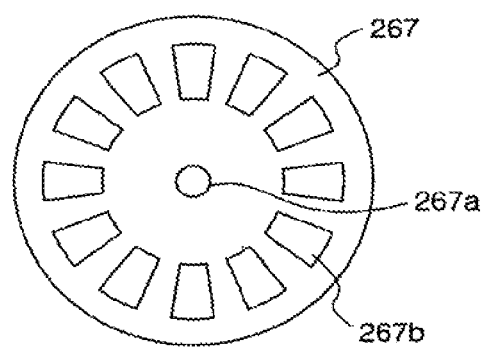
FIG. 13 is a plan view of a main part of the chemical solution administration device according to the fifth embodiment.

In this fifth embodiment, as shown in FIG. 13, the first encoder 267 has twelve holes 267b arranged at regular intervals. The first encoder 267 rotates with rotation of the first motor 265. Then, optical signals that are transmitted through the holes 19b and optical signals that are shielded by the holes 19b are outputted as pulse signals from the first sensor 268. Accordingly, by counting the pulse signals, the number of rotations of the first motor 265, the number of rotations (including rotation angle) of the first shaft 266, and the rotation speeds thereof can be easily measured.

Turning to FIG. 12, reference numeral 269 denotes a first nut that is fixed in conjunction with a piston 280, and an internal thread 269a that fits the external thread 266a formed on the first shaft 266 is provided inside the first nut 269. Accordingly, when the first motor 265 rotates in the positive direction, the rotation of the first shaft 266 cooperates with the first nut 269 to move the piston 280 in the forward direction shown by an arrow 70 (i.e., toward the needle 229 attached). The movement distance of the piston 280 can be measured by counting the pulse signals outputted from the first sensor 268. Further, the movement speed of the piston 280 can be measured by the density (frequency) of the pulse signals outputted from the first sensor 268.

The front end of the piston 280 contacts the stopper 262b that is inserted into the cartridge 228. The stopper 262b is provided slidably from the rear end 228b of the cartridge 228 toward the front end 228a thereof. Accordingly, when the piston moves forward in the direction of the arrow 70, the stopper 262b in the cartridge 228 is pushed in the direction of the arrow 70. That is, the insulin 61 is discharged from the front end of the hollow needle 229. When the first motor 265 is rotated reversely, the piston 280 moves backward in the direction opposite to the arrow 70.

Reference numeral 281 denotes a frame to which the first motor 265 is fixed, and this frame 281 is provided so as to enclose the first motor 265. The first motor 265, the first shaft 266, the first nut 269, the piston 280, the first encoder 267, the first sensor 268, and the extrusion control unit 216a (refer to FIG. 1) constitute an extrusion means 225.

Reference numeral 272 denotes a DC motor, and this second motor 272 is used as a power for reciprocating the frame 281, and the cartridge 228 and the needle 229 that are constituted on the frame 281 are also reciprocated. The second shaft 273 is connected to the rotation axis of the second motor 272. An external thread 273a is formed at the surface of the second shaft 273.

Reference numeral 274 denotes a second encoder that is provided in conjunction with the rotation axis of the second motor 272, and numeral 275 denotes a transmissive sensor for detecting rotation (rotation amount and rotation speed) of the second encoder 274. This second sensor 275 is not necessarily of a transmissive type, and it may be a reflective sensor. Further, like the first encoder 267, the second encoder 274 rotates with rotation of the second motor 272. Then, the rotation information (rotation amount and rotation speed) of the second encoder 274 is outputted from the second sensor 275 as pulse signals. Accordingly, by counting the pulse signals, the number of rotations of the second motor 272, the number of rotations (including rotation angle) of the second shaft 273, and the rotation speeds thereof can be easily measured.

Reference numeral 276 denotes a second nut that is fixed in conjunction with the piston 281, and an internal thread 276a that fits the external thread 273a formed on the second shaft 273 is provided inside the second nut 276. Accordingly, when the second motor 272 rotates in the positive direction, the rotation of the shaft 273 cooperates with the second nut 276, whereby the second nut 276 is moved in the forward direction shown by an arrow 78, that is, the frame 281 is moved in the direction of the arrow 78. The movement distance of the frame 281 can be detected by counting the pulse signals outputted from the second sensor 275. Further, the movement speed of the frame 281 can be detected by the density (frequency) of the pulse signals outputted from the second sensor 275.

When the second motor 272 is rotated in the reverse direction, the second nut 276 moves in the direction opposite to the arrow 78, i.e., moves backward, due to the function of the rotation of the second shaft 273 and the second nut 276. That is, the frame 281 connected to the second nut 276 is moved in the direction opposite to the arrow 78. At this time, the movement distance of the frame 281 can be detected by counting the pulse signals outputted from the second sensor 275. Further, the movement speed of the frame 281 can be detected by the density (frequency) of the pulse signals outputted from the second sensor 275.

To be specific, since the second shaft 273 is connected to the frame 281 through the second nut 276, when the second motor 272 rotates in the positive direction, the frame 281 moves forward in the direction of the arrow 78, whereby the entirety of the extrusion means 225 moves forward. Conversely, when the second motor 272 rotates reversely, the frame 281 moves in the direction opposite to the arrow 78, i.e., moves backward, whereby the entirety of the extrusion means 225 moves backward. In this way, the second motor 272 is rotated in the positive direction or in the reverse direction, whereby the extrusion means 225 and the cartridge 228 and the needle 229 which are included in the extrusion means 225 can be reciprocated.

The second motor 272, the second shaft 273, the second nut 276, the second encoder 274, the second sensor 275, and the reciprocation control unit 217a constitute the reciprocation means 226.

Further, a frame convex portion 281a is formed outward from the frame 281, while a rail 279 to which the frame convex portion 281a fits is formed on the casing 277. Accordingly, the frame convex portion 281a slides on the rail 279. That is, the frame 281 (as well as the cartridge 228 and the needle 229) reciprocates in the direction of the arrow 78 and in the reverse direction, due to the effect of the frame convex portion 281a and the rail 279. At this time, the frame 281 does not rotate with respect to the casing 277 due to the effect of the frame convex portion 281a and the rail 279.

Reference numeral 255 denotes an insertion port from which the blood sensor 111 is inserted, and this insertion port 255 is provided on a wall 277b in the rear of the casing 277 (on the opposite side from the puncture needle port 277a). Reference numeral 255a denotes an insertion path connected to the insertion port 255. Connectors 213~215 to be connected to the terminals 247~249 of the blood sensor 111 are disposed in the back of the insertion path 255a.

During normal operation, the tip of the needle 229 is hidden in the puncture needle port 277a that is formed at the front end of the casing 277. Accordingly, usually the needle 229 is invisible from the outside, thereby reducing patient's fear.

In the chemical solution administration device 212 according to the fifth embodiment of the present invention, since the analytical and mathematical result obtained by the analysis unit 220 is automatically stored as it is in the memory 224, it is not necessary for the patient to enter the dose of the chemical solution using the setting button of the injection device. Further, since the dose is automatically stored in the memory, no setting error occurs, and further, the patient is saved from the burden of setting.

Further, in the chemical solution administration device, since the function of the puncture device for collecting blood, the function of the measurement device for measuring the property of the collected blood, and the function of the injection device for administrating the chemical solution are included in the same casing, the device can be easily taken along. Furthermore, since the needle and the reciprocation means for reciprocating the needle can be shared between correction of blood and administration of chemical solution, miniaturization of the device can be achieved.

Embodiment 6

Figure 14:
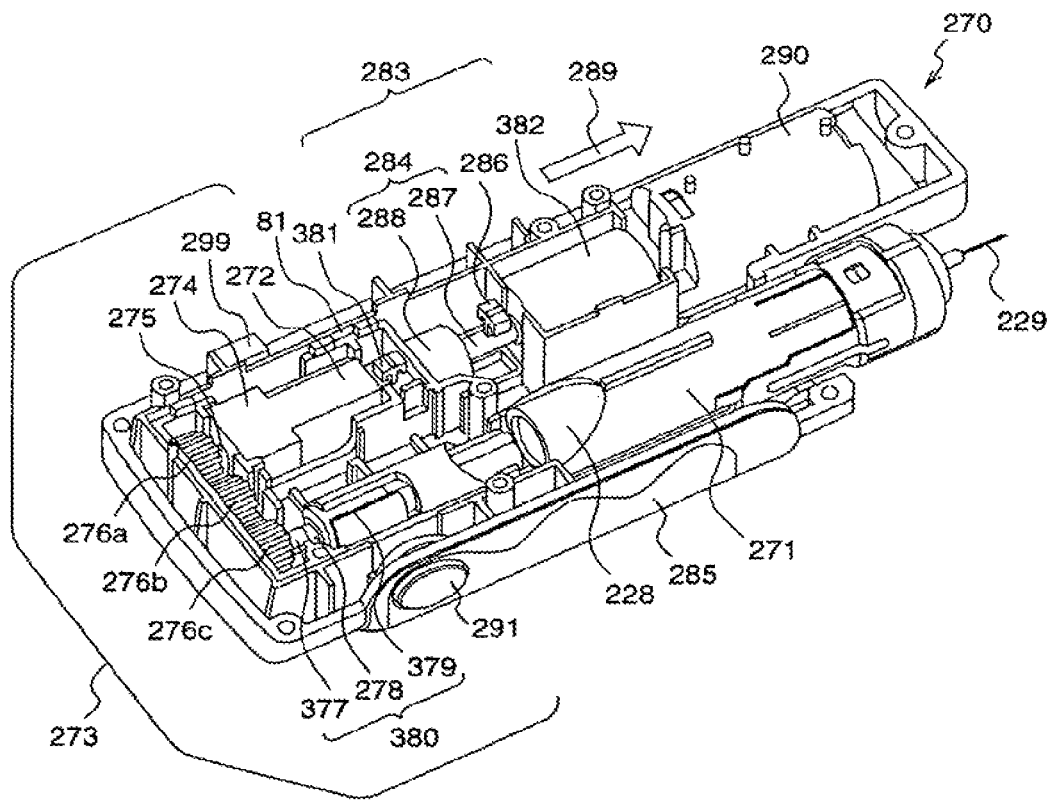
FIG. 14 is an exploded perspective view of a chemical solution administration device according to a sixth embodiment of the present invention.

FIG. 14 is a perspective view illustrating a chemical solution administration device 270 according to a sixth embodiment, with its upper cover being opened. The same reference numerals as those used for the above-mentioned embodiments denote the same elements, and therefore, repeated description is not necessary.

With reference to FIG. 14, reference numeral 228 denotes a cartridge in which insulin 61 is enclosed, and this cartridge 228 is inserted into a cartridge holder 271. Further, reference numeral 229 denotes a needle inserted at a front end of the cartridge 228.

Reference numeral 272 denotes a first motor as a component of an extrusion means 273. Rotation of the first motor 272 is transmitted to a main axis 275 through a deceleration gear 274. The main axis 275 is connected to a first shaft 377 through transmission gears 276a, 276b, 276c. The first shaft 377 is connected to a first nut 379 through an elastic extension member 278. Further, the first nut 379 is fixed in conjunction with the cartridge holder 271. The first shaft 377, the elastic extension member 278, and the first nut 379 constitute a first rpm/linear motion conversion unit 380. Reference numeral 381 denotes a first sensor for measuring the rpm of the first motor 272.

Figure 15:
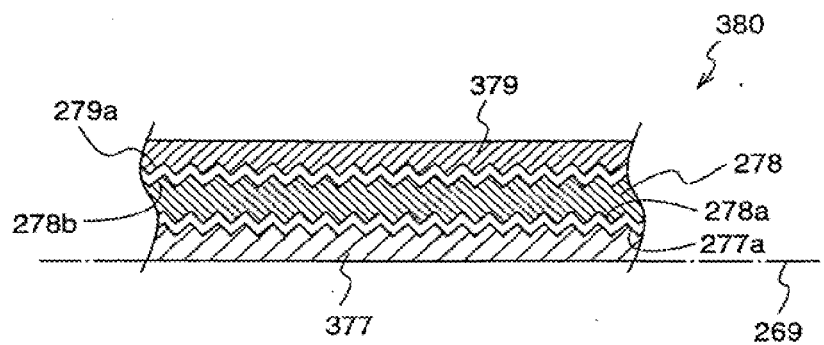
FIG. 15 is a cross-sectional view of a main part of the chemical solution administration device according to the sixth embodiment.

FIG. 15 is a cross-sectional view of a main part of the first rpm/linear motion conversion unit 380 in the chemical solution administration device 270 according to the second embodiment.

With reference to FIG. 15, an external thread 277a is formed at the surface of the first shaft 377. An internal thread 278a that fits the external thread 277a is provided inside the elastic extension member 278, and an external thread 278b is provided on the outer side (surface side) of the elastic extension member 278. An internal thread 279a that fits the external thread 278b is provided inside the first nut 379. Reference numeral 269 denotes a center line of the first shaft 277.

As described above, since the elastic extension member 278 is adopted, the amount of extrusion of the cartridge 228 can be increased while reducing the length of the chemical solution administration device 270. Further, miniaturization of the device can be achieved. Since the first motor 272, the gears 276a, 276b, and 276c, and the first rpm/linear motion conversion unit 380 are arranged in a horseshoe shape, the size of the device in the longitudinal direction can be reduced, resulting in a conveniently portable device.

Reference numeral 382 denotes a second motor as a component of a reciprocation means 283. The second motor 382 is fixed to a casing 285. Reference numeral 286 denotes a second sensor for measuring the rpm of a second shaft 287 connected to the second motor 382. Reference numeral 288 denotes a second nut, and an internal thread 288a is formed inside the second nut 288. An external thread 287a that fits the internal thread 288a is formed at the surface of the second shaft 287, and the second shaft 287 and the second nut 288 constitute a second rpm/linear motion conversion unit 284.

The second nut 288 is connected to a frame 281 that is equipped with the extrusion means 273. The frame 281 is equipped with the extrusion means 273 including the first motor 272, the cartridge 228, and the needle 229, and is slidable with respect to the casing 285. Accordingly when the second motor 382 constituting the reciprocation means 283 is slightly rotated in the positive direction, the extrusion means 273 moves in the direction of an arrow 289, and the needle 229 also moves in the same direction. When the second motor 382 is reversely rotated, the extrusion means 273 moves in the direction opposite to the arrow 89, and the needle 229 moves back into the casing 285.

Reference numeral 299 denotes an insertion port from which the blood sensor 111 is inserted, and this insertion port 299 is provided at a side wall of the casing 285.

Reference numeral 290 denotes a battery serving as a power source for driving the first and second motors 272 and 282 and the like. Reference numeral 291 denotes an administration button for the insulin 61. That is, by pressing the administration button 291, the second motor 282 is positively rotated and thereby the extrusion means 273 is moved in the direction of the arrow 289, and thereafter, the first motor 272 of the extrusion means 273 is positively rotated, whereby the insulin 61 in the cartridge 228 is administered to the patient from the needle 229.

Figure 16:
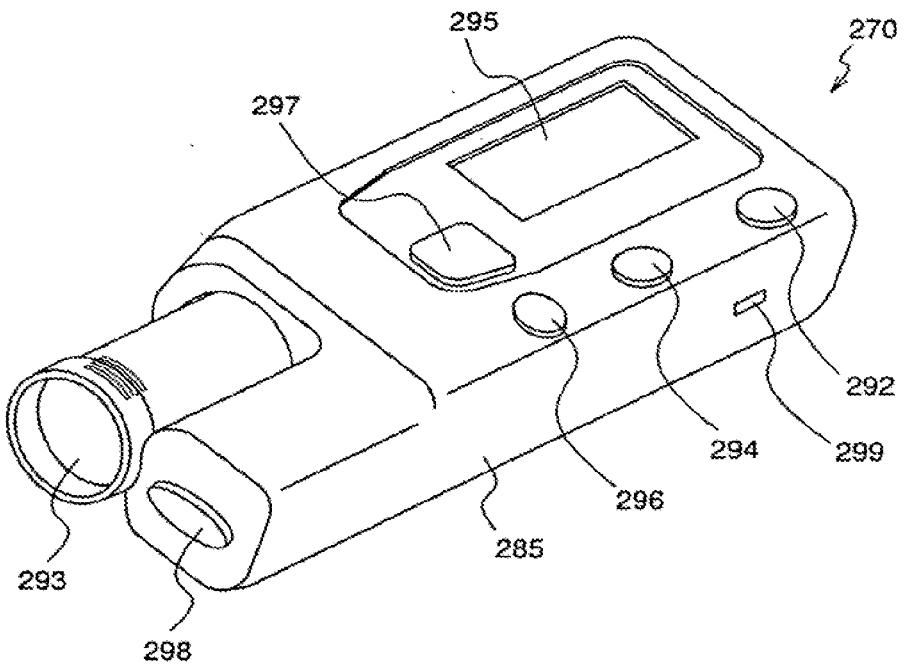
FIG. 16 is an external perspective view of the chemical solution administration device according to the sixth embodiment.
Figure 17:
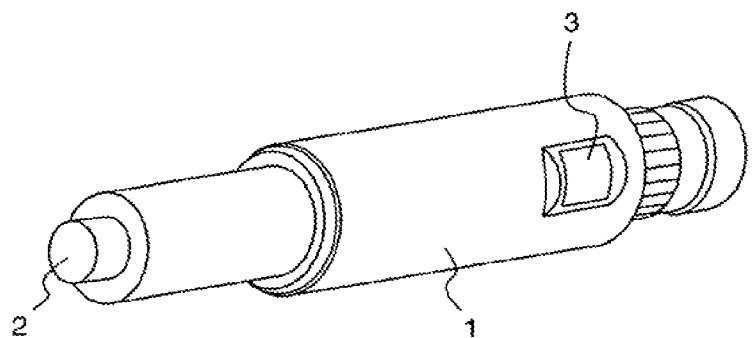
FIG. 17 is an external perspective view of a conventional puncture device.
Figure 18:
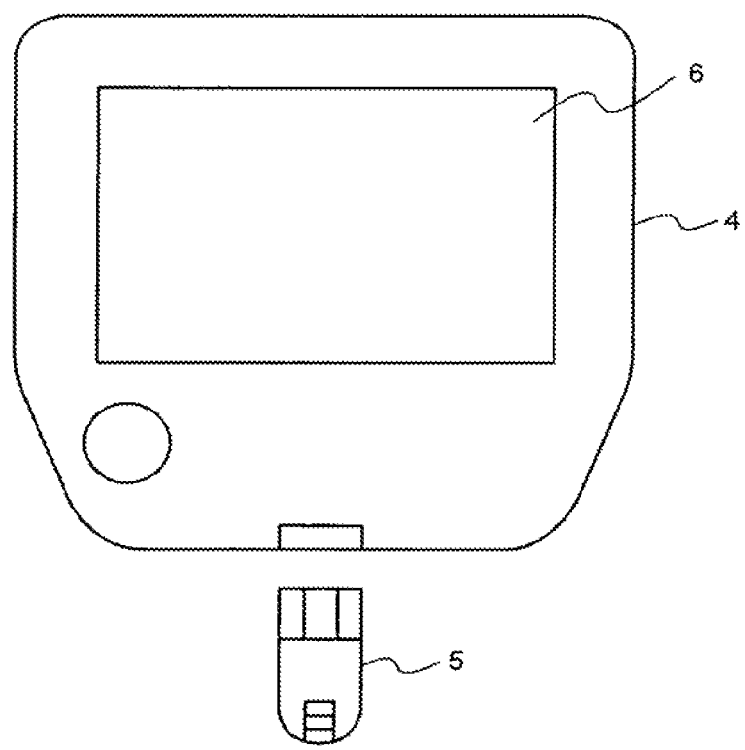
FIG. 18 is a plan view of a sensor and a measurement device included in a conventional puncture device.

FIG. 16 is an external perspective view of the chemical solution administration device 270 according to the sixth embodiment. In FIG. 16, reference numeral 292 denotes a puncture button. When the puncture button 292 is pressed, the needle 229 protrudes from the puncture needle port 293, whereby puncture or administration of insulin 61 is carried out. Reference numeral 294 denotes a setting button, and the amount of insulin 61 to be administered is adjustable using the setting button 294. The set value is displayed on a display unit 295.

Also in this sixth embodiment, like the fifth embodiment, this setting button 294 is used only when it is desired to set a dose of insulin that is different from the automatically set dose of insulin, on the basis of the data of measured blood glucose level.

Reference numeral 296 denotes an air releasing button, and the air in the cartridge 228 and the needle 229 can be removed by pressing the air releasing button 296. Reference numeral 297 denotes a power supply switch that is provided in approximately the center of the casing 285 and next to the display unit 295. Since the respective buttons are arranged in the positions mentioned above, it is avoided that the power supply is turned off by mistake during the operation.

Reference numeral 298 denotes a touch sensor which is provided next to the puncture needle port 293. Accordingly, when performing puncture or administration of insulin 61, since the touch sensor 298 spontaneously touches the skin of the patient to sense the skin, the burden of operation can be reduced. Further, when performing air releasing, since the touch sensor 298 is spontaneously separated from the skin and therefore it does not sense the skin, thereby ensuring safety.

Reference numeral 299 denotes an insertion port from which the blood sensor 111 is inserted, which is provided on the side wall in the rear of the casing 285 (on the side wall adjacent to the touch sensor 298). An insertion path is provided in conjunction with the insertion port 299, and connectors 213, 214, and 215 to be connected to the terminals 119, 120, and 118 of the blood sensor 111, respectively, are provided at the back of the insertion path.

In the chemical solution administration device 270 according to the sixth embodiment of the present invention, the analytical and arithmetical result analyzed by the analysis unit 220 is automatically stored as it is in the memory 224, it is not necessary for the patient to enter a desired setting using the setting button of the injection device. Moreover, since the analyzed result is automatically restored in the memory 224, there occurs no setting error.

Further, since the result is automatically stored in the memory 224, the patient is saved from the burden of setting.

Furthermore, since the function of the puncture device for collecting blood, the function of the measurement device for measuring the property of the collected blood, and the function of the injection device for administrating the chemical solution are integrated in the same casing, the device can be easily taken along.

Moreover, since the needle and the reciprocation means for reciprocating the needle can be shared between correction of blood and administration of chemical solution, miniaturization of the device can be achieved.

APPLICABILITY IN INDUSTRY

Since an injection device with puncture function according to the present invention can be easily taken along, it is useful as a portable injection device with puncture function.

What is claimed is:

1. An injection device with puncture function, comprising:
a cartridge having a chemical solution enclosed therein, a front end, and a needle inserted in the front end;
a cartridge holder into which the cartridge is inserted;
a reciprocation unit configured to reciprocate the cartridge and the cartridge holder; and
an extrusion member configured to extrude the chemical solution from a rear end of the cartridge toward the needle, said extrusion member including:
a motor,
a rotation/linear motion conversion unit which is disposed between a rotation axis of the motor and a piston that pushes the rear end of the cartridge, and
a rpm detection unit for detecting a rpm of the motor;
wherein the reciprocation unit is configured to vary a motion speed and an amount of motion of the reciprocation unit while reciprocating the cartridge and while puncture by the needle or administration of the chemical solution through the needle is carried out.

2. An injection device with puncture function as defined in claim 1, wherein said rotation/linear motion conversion unit includes:
a shaft having an external thread at a surface thereof, and
a baffle-shaped unit to which a nut having an internal thread that fits the external thread is fixed, the baffle-shaped unit being formed integrally with the piston.

3. An injection device with puncture function as defined in claim 1, wherein the rpm detection unit includes:
an encoder connected to a rotation axis of the motor, and
a sensor for detecting a rpm of the encoder.

4. An injection device with puncture function as defined in claim 2, wherein an elastic extension member is inserted between the shaft and the nut.

5. An injection device with puncture function as defined in claim 1, wherein said motor, said rotation/linear motion conversion unit, and a plurality of gears provided between the motor and the rotation/linear motion conversion unit are arranged in a horseshoe shape.

6. An injection device with puncture function, comprising:
a cartridge having a chemical solution enclosed therein, a front end, and a needle inserted in the front end;
a cartridge holder into which the cartridge is inserted;
a reciprocation unit configured to reciprocate the cartridge and the cartridge holder, the reciprocation unit including:
a motor,
a rotation/linear motion conversion unit which is connected between a rotation axis of the motor, and a rear end of a frame on which the extrusion member is mounted, and
a rpm detection unit for detecting a rpm of the motor; and
an extrusion member configured to extrude the chemical solution from a rear end of the cartridge toward the needle;
wherein the reciprocation unit is configured to vary a motion speed and an amount of motion of the reciprocation unit while reciprocating the cartridge and while puncture by the needle or administration of the chemical solution through the needle is carried out.

7. An injection device with puncture function as defined in claim 6, wherein said rotation/linear motion conversion unit includes:
   a shaft having an external thread at a surface thereof, and
   a frame to which a nut having an internal thread that fits the external thread is fixed.

8. An injection device with puncture function as defined in claim 6, wherein the rpm detection unit includes:
   an encoder that is connected to the rotation axis of the motor, and
   a sensor for detecting a rpm of the encoder.

9. An injection device with puncture function as defined in claim 1, further comprising a power supply switch configured to turn a power supply on and off, the power supply switch being disposed in approximately a center of a casing of the injection device.

10. An injection device with puncture function, comprising:
   a cartridge having a chemical solution enclosed therein, a front end, and a needle inserted in the front end;
   a cartridge holder into which the cartridge is inserted;
   a reciprocation unit configured to reciprocate the cartridge and the cartridge holder; and
   an extrusion member configured to extrude the chemical solution from a rear end of the cartridge toward the needle;
   wherein the reciprocation unit is configured to vary a motion speed and an amount of motion of the reciprocation unit while reciprocating the cartridge and while puncture by the needle or administration of the chemical solution through the needle is carried out; and
   wherein the injection device is configured to communicate with a measurement device that measures a blood glucose level, data of the measured blood glucose level, using a communication unit.

11. An injection device with puncture function as defined in claim 10, wherein the communication unit is configured to perform communication using light.

12. An injection device with puncture function as defined in claim 1, wherein the reciprocation unit includes a magnet, a coil, and a linear encoder.

13. An injection device with puncture function as defined in claim 1, wherein said reciprocation unit includes:
   a magnet;
   a coil; and
   a guide pin configured to guide a frame on which the extrusion member is disposed so as to move the frame linearly,
   wherein the magnet and the coil are configured to drive the frame so as to move the frame linearly, the magnet and the coil being attached onto an outer circumference of the frame, and
   a linear encoder configured to detect a movement distance of the frame.

14. A method for controlling an injection device with puncture function, which controls the puncture operation of the injection device with puncture function defined in claim 1, said method comprising:
   a first step of moving the needle forward at a high speed by a small distance, using the reciprocation unit;
   a second step of moving the needle backward to its original position at a high speed, using the reciprocation unit, after the first step;
   a third step of setting an amount of extrusion of the chemical solution, after the second step;
   a fourth step of moving the needle forward at a low speed by a large distance, using the reciprocation unit, after the third step;
   a fifth step of extruding the chemical solution from the needle by the amount that is set in the third step, using the extrusion member, after the fourth step; and
   a sixth step of moving the needle backward to its original position at a low speed, using the reciprocation unit, after the fifth step.

15. The method for controlling an injection device with puncture function as defined in claim 14, further including:
   a seventh step of moving the needle forward at a low speed by a large distance using the reciprocation unit, between the third step and the fourth step;
   an eighth step of extruding air in the cartridge from the needle using the extrusion member, after the seventh step; and
   a ninth step of moving the needle backward to its original position at a low speed using the reciprocation unit, after the eighth step.

* * * * *